United States Patent [19]

Iwasaki et al.

[11] Patent Number: 5,376,214
[45] Date of Patent: Dec. 27, 1994

[54] ETCHING DEVICE

[75] Inventors: Yasukazu Iwasaki, Yokosuka; Makoto Uchiyama, Miura, both of Japan

[73] Assignee: Nissan Motor Co., Ltd., Yokohama, Japan

[21] Appl. No.: 118,203

[22] Filed: Sep. 9, 1993

[30] Foreign Application Priority Data

Sep. 22, 1992 [JP] Japan .................................. 4-252544
Sep. 22, 1992 [JP] Japan .................................. 4-252891

[51] Int. Cl.$^5$ ........................ H01L 21/306; B44C 1/22
[52] U.S. Cl. .................................. 156/345; 156/637
[58] Field of Search ............... 156/345, 626, 627, 637, 156/639, 642, 656, 657, 659.1, 662; 252/79.2, 79.3, 79.4; 204/129.1, 129.2, 129.5, 129.65

[56] References Cited

U.S. PATENT DOCUMENTS

| | | | |
|---|---|---|---|
| 3,874,959 | 4/1975 | Hoekstra et al. | 204/129.2 X |
| 3,890,215 | 6/1975 | DiLorenzo et al. | 204/129.2 X |
| 3,959,098 | 5/1976 | Schwartz | 204/129.3 |
| 5,129,981 | 7/1992 | Wang et al. | 156/662 X |
| 5,173,149 | 12/1992 | Nojiri et al. | 156/627 |
| 5,266,152 | 11/1993 | Iwasaki et al. | 156/627 X |

FOREIGN PATENT DOCUMENTS 49-45035 12/1974 Japan .
3-261948 11/1991 Japan .

OTHER PUBLICATIONS

H. Muraoka, et al.—Controlled Preferential Etching Technology, pp. 327–338, The Electrochemical Society Softbound Sump., 1973.

Primary Examiner—William Powell
Attorney, Agent, or Firm—Foley & Lardner

[57] ABSTRACT

An etching device performing an etching process on a material immersed in a etchant which is a mixture of acids of which the main components are fluoric acid, nitric acid, and acetic acid. The etching device includes a semiconductor electrode immersed in the etchant, an opposing electrode immersed in the etchant, an electron meter for detecting an electric potential difference between the semiconductor electrode and the opposing electrode, and a controller for uniformly controlling the nitrite ion concentration in the etchant from the electric potential difference between the semiconductor electrode and the opposing electrode, detected by the electronmeter.

18 Claims, 19 Drawing Sheets

ETCHING DEVICE

TECHNICAL FIELD

The present invention relates to an etching device, and, in particular, to an etching device capable of carrying out an etching process having a stable etching characteristic.

BACKGROUND ART

Conventionally, silicon is selectively etched using a mixture of acids comprising fluoric acid, nitric acid, and acetic acid. Dash has developed a method for evaluating defects in silicon using an etchant made up of a 1:3:12 volumetric ratio of these acids.

A later etching method has been proposed using an etchant with a volumetric ratio of these acids of 1:3:8.

Because the etching rate of this etching method depends on the concentration of impurities in the crystals, the etchant has been attracting attention as an isotropic selective etchant.

However, there is the problem that the etching characteristics of this selective etchant have a tendency to change, causing poor controllability. Accordingly, Muraoka et al. have proposed a method for controlling selectivity by the addition of a hydrogen peroxide solution into tile etchant (Japanese Laid Open Patent Application 49-45035).

An example of an etching device using the method of Muraoka et al. is described in the following two papers:

"CONTROLLED PREFERENTIAL ETCHING TECHNOLOGY", H. Muraoka, T. Ohhashi, and Y. Sumitomo, Semiconductor Silicon 1973, the Electrochem. Soc., Soft-Bound Symposium, Sir Princeton N.J., H. R. Huff and R. R. Burgess, eds., Electrochem. Soc.; pp 327 to 338, 1973".

In this device, an etchant made up of fluoric acid, nitric acid, and acetic acid (volumetric ratio 1:3:8) is filled into an etching tank and continuously agitated using a stirring bar, while an object of the etching process, such as a silicon substrate or the like held by a jig, is etched.

In this device, the concentration of nitrite ions formed as the result of a dissolution reaction with the etchant is monitored using an electron meter by measuring the electric potential between a pair of electrodes, specifically a platinum electrode and a carbon electrode, immersed in the etchant.

The concentration of the above-mentioned nitrite ions must be uniformly controlled during the etching process from start to finish so that the etching characteristics of the etchant do not change. In this method, a reagent, for example, a hydrogen peroxide solution, is added to oxidize the nitrite ions so that the potential between the electrodes is kept uniform.

The inventors of the present invention have also proposed a method of etching process in which nitrite acid or a chemical which produces nitrite ions is added to the processing liquid. (Japanese Patent Application 3-261948 and Summary of Lectures of the 1991 Electrochemical Autumn Conference (the site of the meeting is Nagoya in Japan), No. 2H25, Page 174, "Micromachining of Silicon by means of Isotropic Selective Etching."

However, in this conventional method of etching process, a metal electrode such as platinum or gold and a carbon electrode are directly immersed in the etchant. Therefore, when monitoring the etchant using such conventional methods, the monitor electrode, which is the platinum electrode or the gold electrode, is dissolved by the etchant and is mixed with the etchant, and this leads to the danger that the material to be etched will be contaminated by the metal.

This type of metal contamination is a problem because the life expectancy of the silicon is reduced, or the like. Therefore, there is the problem that the adjustability of the semiconductor fabricating process, which requires a high degree of cleanliness, is not good.

For example, when a platinum electrode and a gold electrode are used, about 4 ppb of gold are detected when the used etchant is analyzed in a graphite furnace analysis method.

In addition, a uniform nitrite ion concentration is maintained in the conventional method by adding a hydrogen peroxide solution to the etchant, and the characteristic of the electric potential difference between monitor electrodes and the characteristic of the ion concentration of the etchant are affected in both regions, a plateau region (or a flat region) and a jump region.

The hydrogen peroxide solution is added in this plateau region, and even when the ion concentration is reduced no change is observed in the electric potential difference, therefore the etchant is not monitored in this plateau region.

Accordingly, the monitoring must be set so that this detection is made in the jump region.

For example, when the platinum and the gold electrodes are used, if the concentration of the nitrite ions slightly exceeds 100 ppm (converted to nitrite ions, including chemicals formed from the nitrite ions by means of a reaction in equilibrium) the process has already entered the plateau region and the electric potential between the electrodes still does not change for a change in the nitrite ion concentration. For this reason, it is not possible to estimate the nitrite ion concentration in the plateau region, and there is no process monitor function.

Because metal electrodes and the like are immersed in the etchant when this type of conventional monitoring process is used, the danger of fouling is high and it becomes impossible to measure the correct nitrite ion concentration In addition, even using this method based on the conventional etching device, in tests dealing with three-dimensional micro-machining of an intelligent sensor representative of a manufacturing process for an acceleration sensor, the etching reaction did not proceed to completion, so specifically, there was the problem that the etching did not proceed to completion.

For example, a conventional method, in which a hydrogen peroxide solution is added to an etchant to maintain a uniform nitrite ion concentration in the liquid, cannot be applied in the case where the etching reaction is out of control.

In general, the nitrite ion concentration is increased after starting the etching process. But, in a micro-machining representative intelligent sensor process, the nitrite ions are dispersed and diffused in the etchant, so that the nitrite ion concentration is seen to decrease.

SUMMARY OF THE INVENTION

Accordingly, an object of the present invention is to provide, with due consideration to the drawbacks of such conventional etching devices, an etching device wherein, as the result of using a semiconductor electrode of silicon or the like which is the same material as an object material to be etched, the etchant is not contaminated, and the monitored results are highly accurate.

Another object of the present invention is to provide, an etching device wherein stable micro-machining of high precision can be carried out during a wet process such as a washing process, an etching process, or the like, using a mixture of acids in which the main components are fluoric acid and nitric acid, as a processing liquid.

According to an aspect of the present invention, an etching device performing an etching process on a material immersed in the processing liquid, using a processing liquid which is a mixture of acids of which the main components are fluoric acid, nitric acid, and acetic acid, the etching device comprises:

a semiconductor electrode immersed in the processing liquid;

an opposing electrode which is also immersed in the processing liquid, opposing said semiconductor electrode;

means for detecting an electric potential difference between said semiconductor electrode and said opposing electrode; and control means for uniformly controlling the nitrite ion concentration in the processing liquid from the electric potential difference between said semiconductor electrode and said opposing electrode, detected by said detection means.

In the etching device described above said semiconductor electrode comprises a silicon electrode and said opposing electrode comprises a platinum electrode.

In the etching device described above said semiconductor electrode comprises a silicon electrode and said opposing electrode comprises a carbon electrode.

According to another aspect of the present invention, an etching device performing an etching process on a material immersed in the processing liquid, using a processing liquid which is a mixture of acids of which the main components are fluoric acid, nitric acid, and acetic acid, the etching device comprises:

a semiconductor electrode immersed in the processing liquid;

an opposing electrode which is also immersed in the processing liquid, opposing said semiconductor electrode;

means for detecting an electric potential difference between said semiconductor electrode and said opposing electrode; and chemical addition means for adding nitrite ions or a chemical which generates nitrite ions to the processing liquid corresponding to the electric potential difference between said semiconductor electrode and said opposing electrode, detected by the detection means.

In the etching device described above, said semiconductor electrode comprises a silicon electrode and said opposing electrode comprises a platinum electrode.

In the etching device described above, said semiconductor electrode comprises a silicon electrode and said opposing electrode comprises a carbon electrode.

According to another aspect of the present invention, an etching device performing an etching process on a material immersed in the processing liquid, using a processing liquid which is a mixture of acids of which the main components are fluoric acid, nitric acid, and acetic acid, the etching device comprises:

a semiconductor electrode to which a voltage is applied, immersed in the processing liquid;

an opposing electrode which is also immersed in the processing liquid, opposing said semiconductor electrode;

electric potential difference detection means for detecting an electric potential difference between said semiconductor electrode and said opposing electrode; and voltage control means for controlling the voltage applied to said semiconductor electrode, corresponding to the electric potential difference between said semiconductor electrode and said opposing electrode, detected by said electric potential difference detection means.

In the etching device described above, said semiconductor electrode comprises a silicon electrode.

In the etching device described above, said voltage control means applies the voltage to said semiconductor electrode in order to dissolve said semiconductor electrode into the processing liquid corresponding to the electric potential difference between said semiconductor electrode and said opposing electrode detected by said electric potential difference detection means.

According to another aspect of the present invention, an etching device performing an etching process on a material immersed in the processing liquid, using a processing liquid which is a mixture of acids of which the main components are fluoric acid, nitric acid, and acetic acid, the etching device comprising:

absorption detection means for detecting the absorption of the processing liquid; and control means for uniformly controlling the nitrite ion concentration in the processing liquid corresponding to the absorption of the processing liquid detected by said absorption detection means.

in the etching device described above, said absorption detection means comprises a spectrophotometer.

According to another aspect of the present invention, an etching device performing an etching process on a material immersed in the processing liquid, using a processing liquid which is a mixture of acids of which the main components are fluoric acid, nitric acid, and acetic acid, the etching device, comprises:

absorption detection means for detecting the absorption of the processing liquid; and chemical addition means for adding nitrite ions or a chemical which generates nitrite ions to the processing liquid corresponding to the absorption of the processing liquid detected by said absorption detection means.

In the etching device described above, said absorption detection means comprises a spectrophotometer.

BRIEF DESCRIPTION OF THE DRAWINGS

These and other objects, features, and advantages of the present invention will become more apparent from the following description of the preferred embodiments taken in conjunction with the accompanying drawings, in which.

DETAILED DESCRIPTION OF THE PREFERRED EMBODIMENTS

Other features of this invention will become apparent in the course of the following description of exemplary embodiments which are given for illustration of the invention and are not intended to be limiting thereof.

A first embodiment of an etching device 100 according to the present invention will now be explained in detail, with reference to the drawings.

Figure 1:
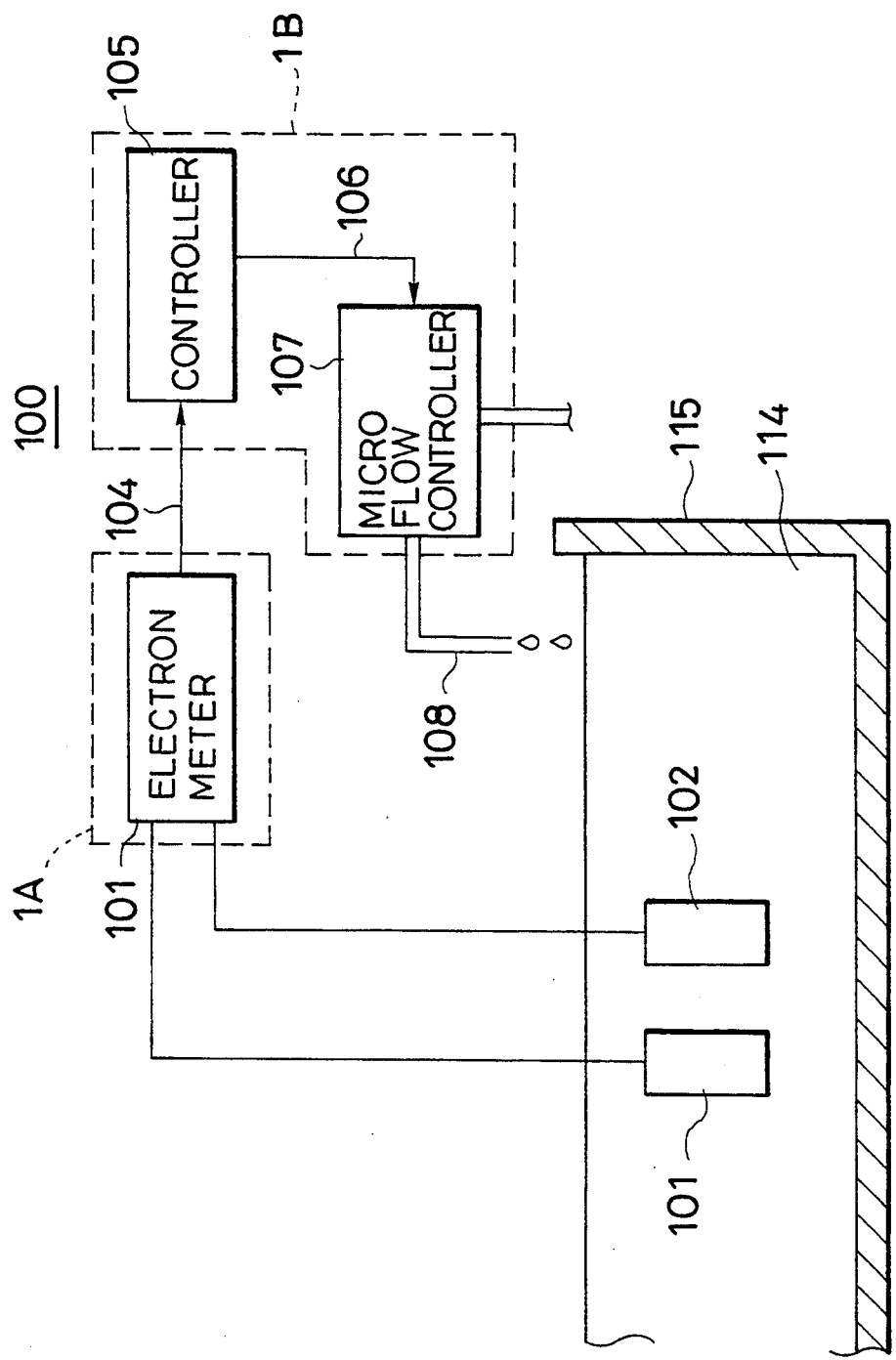
FIG. 1 is a diagram illustrating a first embodiment of an etching device of the present invention.

A monitoring device 1A, comprising a silicon electrode 101 and a platinum electrode 102 immersed in an etching tank 115 filled with an etchant 114, and an etching control device 1B for adding a nitrite solution according to the result detected by the monitoring device 1A, are mounted on this etching device, as illustrated in FIG. 1, which has the special feature that etching is carried out while the nitrite solution is added so that the normally desired value of the nitrite ion concentration is maintained.

The monitoring device 1A detects changes in the nitrite ion concentration in the etching tank 115 by detecting the NOx concentration in the etching tank 115 as an electric potential difference between the silicon electrode 101 and the platinum electrode 102.

When a drop in the nitrite ion concentration is detected by the monitoring device 1A, a controller 105 of the etching control device 1B transmits a control signal 106 to a micro flow controller 107. The micro flow controller 107 controls a volume of a trace of solution to be added. Then, the nitrite solution is added to the etching tank 115 through a nozzle 108 based on the control signal 106. Specifically, when a drop in the nitrite ion concentration of the etchant 114 is detected by the monitoring device 1A, the controller 105 controls the micro flow controller 107 so that the nitrite solution is added. Then, when the nitrite solution is added into the etchant 114, the nitrite ion in the etchant 114 is replenished. When the monitoring device 1A determines that the nitrite ion concentration in the etchant 104 has reached an optimum value, the controller 105 controls the micro flow controller 107 so that the replenishment of the nitrite ion is halted.

Figure 2:
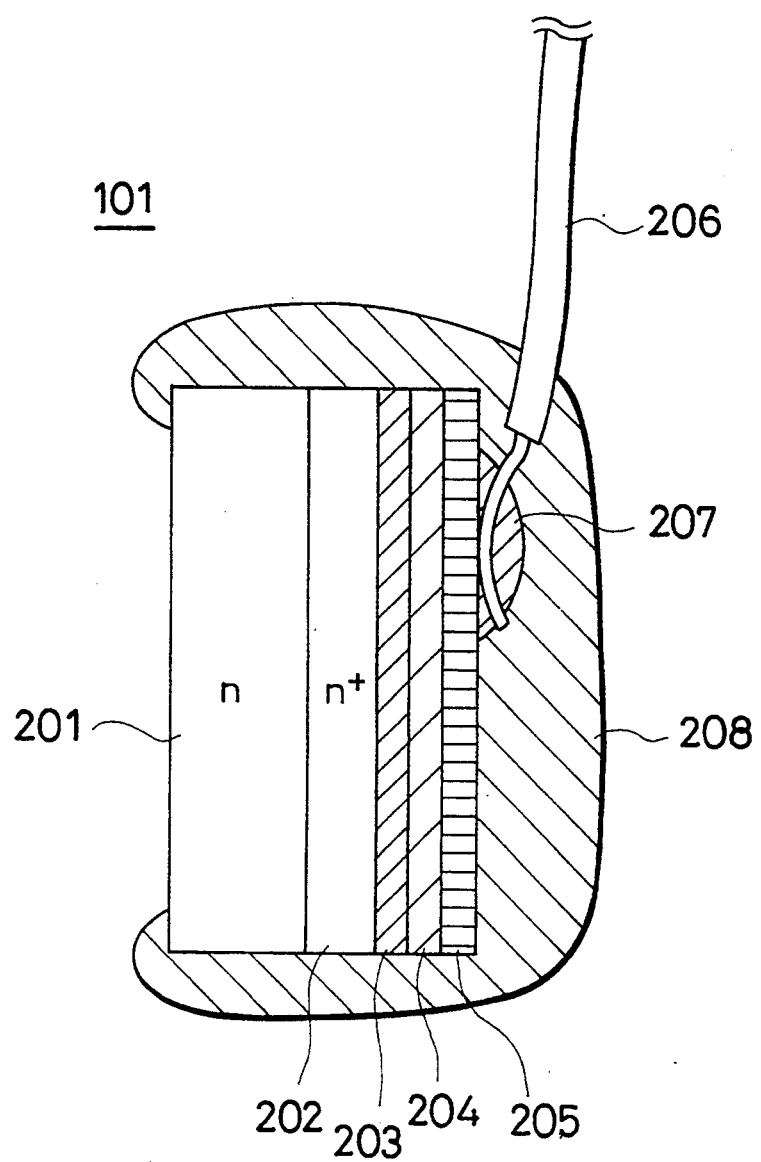
FIG. 2 is a diagram illustrating a silicon electrode for the etching device shown in FIG. 1.

The silicon electrode 101, as illustrated in FIG. 2, comprises an n type silicon substrate 201 with an n+ type diffusion layer 202 as a contact layer, a vapor deposited Ti layer 203 as an adhesion layer and a vapor deposited Ni layer 204 as a barrier layer, a vapor deposited Ag layer 205 as a soldered terminal, and a lead 206 connected to the vapor deposited Ag layer 205 using solder 207. The region is covered by a resin layer 208 with the exception of the silicon substrate surface.

During the fabrication process of the silicon electrode 101, arsenic ions are implanted on the bottom surface of the n type silicon substrate 201 of a comparative resistance of 10 $\Omega$cm at a surface indices or Miller indices (100), an annealing process as a heat processing is performed, and the n+ type diffusion layer 202 is formed as the contact layer. The vapor deposited Ti layer 203 as an adhesion layer, the vapor deposited Ni layer 204 as a barrier layer, and the vapor deposited Ag layer 205 as a soldered terminal are then successively deposited on the upper surface of the n+ type diffusion layer 202. The vapor deposited Ag layer 205 is then connected to the lead 206 by the solder 207, and the region is covered by a resin layer 208 with the exception of the silicon substrate surface.

Figure 3:
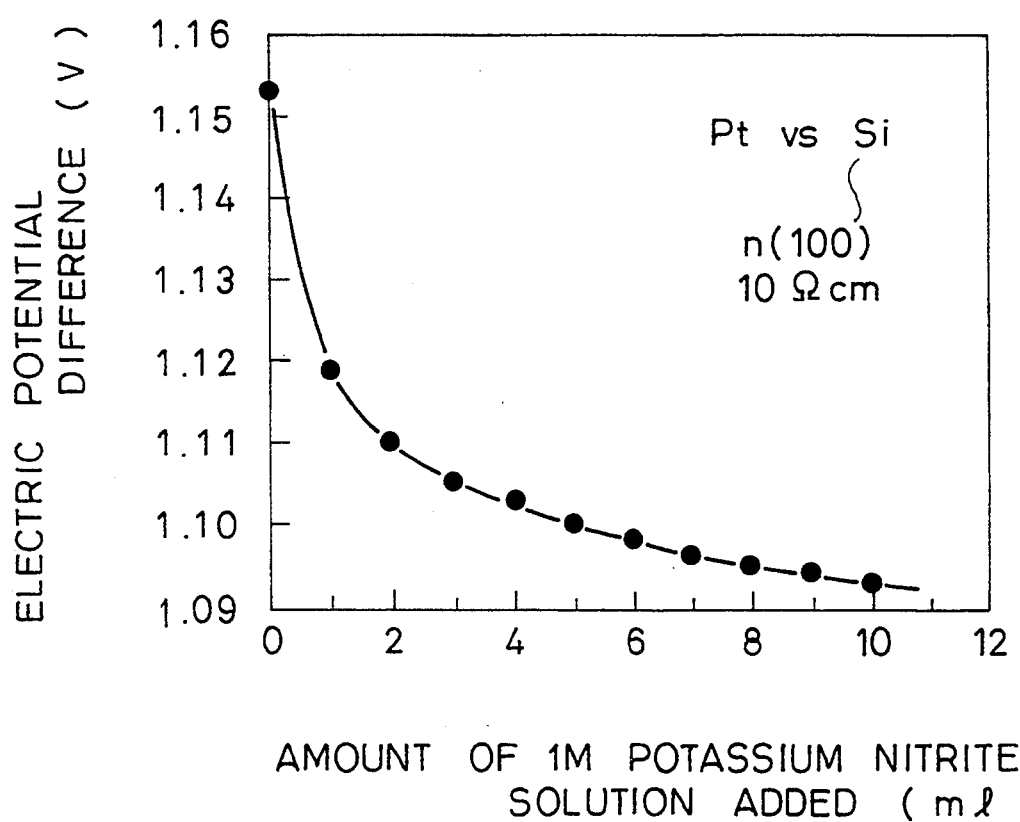
FIG. 3 is a graph showing the relationship between the electric potential difference and the amount of potassium nitrite solution added, using a silicon electrode (n type) and a platinum electrode in the etching device shown in FIG. 1.

The relationship between the electric potential difference between the silicon electrode 101 and the platinum electrode 102 and the amount of potassium nitrite added to the etchant 114 is shown in FIG. 3.

As clearly shown in this drawing, there is no plateau region and the changes are very smooth. This is a highly superior process monitor. As between silicon and platinum, silicon is dissolved into the etchant as high as the platinum. The silicon electrode 301 therefore is dissolved into the etchant 114.

As a result, the danger of the etchant becoming contaminated with heavy metals or the like is low, and the adjustability of the semiconductor fabricating process, which requires a high degree of cleanliness, is good.

Furthermore, there is a proportional relationship between the amount of potassium nitrite added to the etchant and the nitrite ion concentration.

Figure 4:
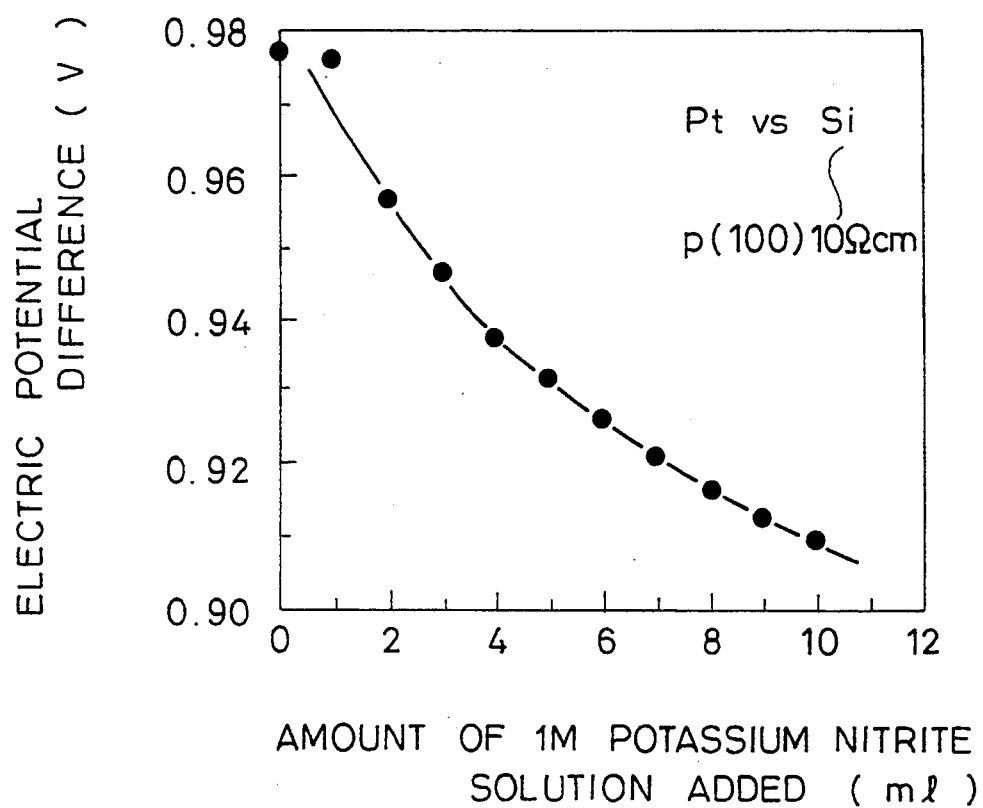
FIG. 4 is a graph showing the relationship between the electric potential difference and the amount of potassium nitrite solution added, using a silicon electrode (p type) and a platinum electrode in the etching device shown in FIG. 1.

The above-mentioned embodiment was explained for an example in which an n type silicon was used as the electrode, however, this invention is not limited to the scope of the embodiment described above. For example, a p-type silicon could also be used as an electrode instead of the silicon electrode 104. In such a case, instead of implantation of arsenic ions, a p+ diffusion layer is formed by a $BBr_3$ deposition. The relationship between the electric potential difference between the silicon electrode and the platinum electrode and the amount of potassium nitrite ions added to the etchant at this time is given in FIG. 4.

As clearly shown in this graph, there is no plateau region and the changes are very smooth. This is a highly superior process monitor. Also, another noble metal, other than platinum, or a carbon electrode or the like may be used.

Figure 5:
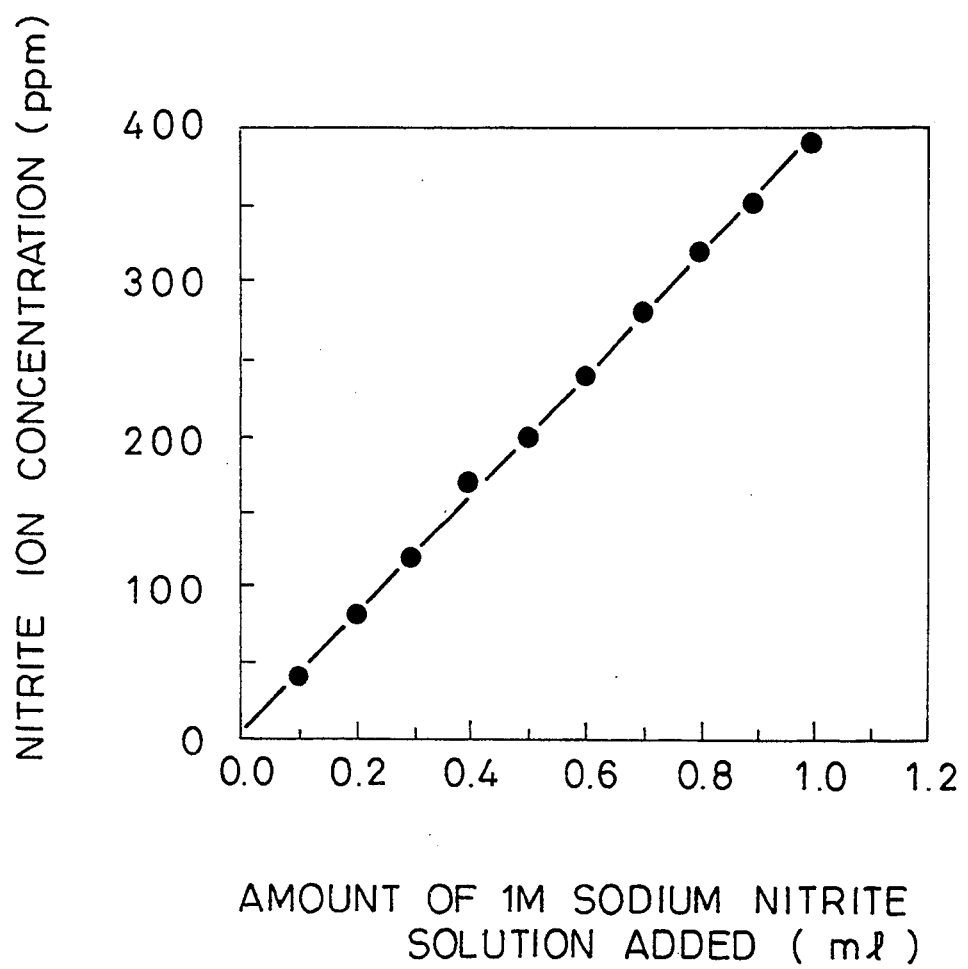
FIG. 5 is a graph showing the relationship between the nitrite ion concentration and the amount of potassium nitrite solution added, in the etching device shown in FIG. 1.

Next, FIG. 5 illustrates the result of the measurement of the change of nitrite ion concentration when sodium nitrite was added to the etchant, in order to confirm the relationship between the amount of sodium nitrite or potassium nitrite added to the etchant and the nitrite ion concentration. The etchant used in this case was a so-called isotropic etchant which is a mixture of a 49 wt % fluoric acid (used in the electronic industry), a 61 wt % nitric acid (used in the electronic industry), and a 99.5% acetic acid (special grade) in the volumetric ratio of 1:3:8. 100 ml of this etchant was placed in a series of beakers and doses of 0.1, 0.2, . . . up to 1.0 ml of sodium nitrite solution (1 mol/lt) were added to the beakers in turn.

After one minute a 0.1 ml sample was taken from each beaker and the nitrite ion concentration was measured using a calorimetric method. The method of measuring the nitrite ion concentration using colorimetry involves masking the fluoric acid in the etchant using boric acid, diazotization of sulfanilic acid by the sulfite ions in the etchant, and coupling α-naphthylamine, to form 4-amino-1-naphthylazobenzene-p-sulfonic acid, then performing an absorption measurement at 545 nm. Here, the fluoric acid is masked with boric acid in order to allow normal absorption measurement by means of a quartz cell and to prevent the fusion of the cell itself. Specifically, when the fluoric acid is masked as tetrafluoroboric acid using boric acid, the tetrafluoroboric acid is a compound in colorless solution, and does not dissolve the quartz in this state.

In addition, the tetrafluoroboric acid is not influenced by the absorption of the color. Further, the standard nitrite solution is adjusted, and the nitrite ion concentration of the etchant is estimated by means of a calibration curve method. The result is shown in FIG. 5 with the nitrite ion concentration shown as linear in the range from 0 to 400 ppm. Accordingly, adding a nitrite solution is an appropriate method for adjusting the nitrite ion concentration.

Figure 6:
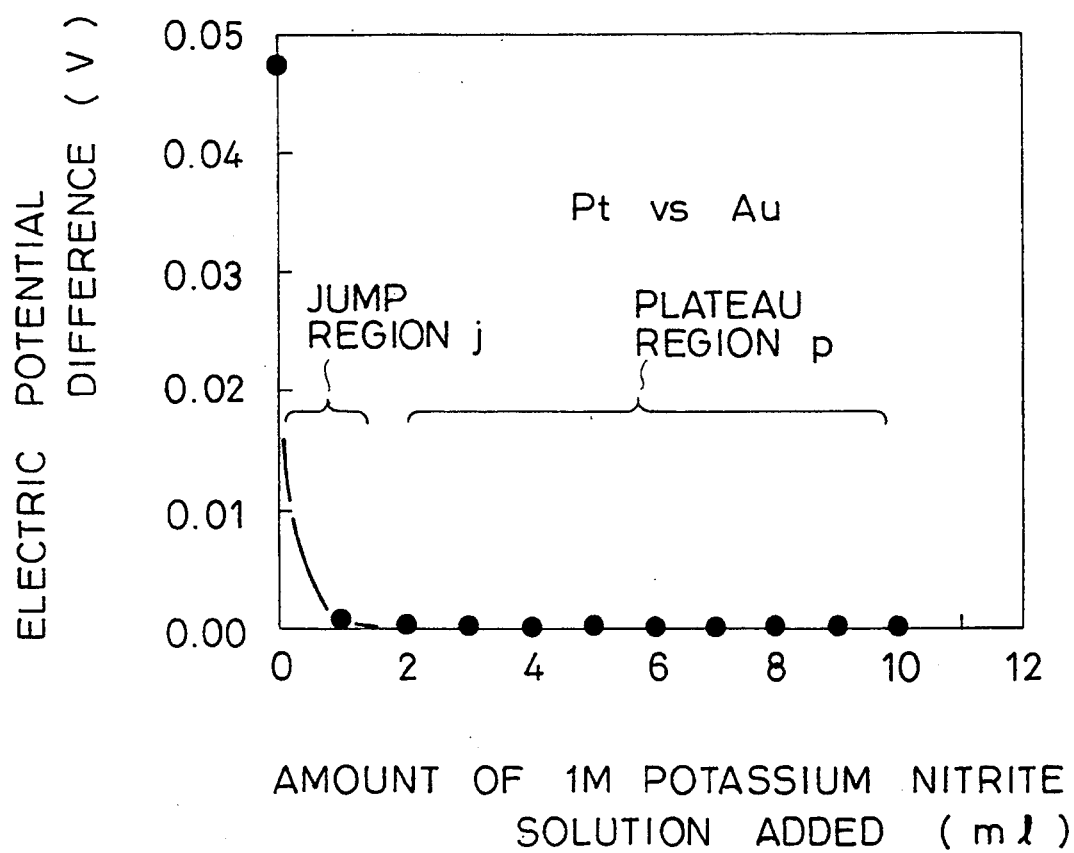
FIG. 6 is a graph showing the relationship between the electric potential difference and the amount of potassium nitrite solution added, using a platinum electrode and a gold electrode in a conventional etching device.

For comparison, the results of measuring the nitrite ion concentration when a platinum electrode and a gold electrode are used as a monitor are shown in FIG. 6.

This drawing shows the results of measuring the relationship between the amount of potassium nitrite solution added and the difference in the potential when 1.2 liter of the above-mentioned isotropic etchant was placed in a beaker and agitated using a magnetic stirrer, then the potassium nitrite solution was added.

As can be readily understood from this graph, a jump region j and a plateau region p are formed, and good monitoring characteristics cannot be demonstrated.

Next, an explanation will be given for carrying out shape machining process of abeam section of a pressure sensor during selective etching of a silicon substrate using this etching device.

Figure 7A:
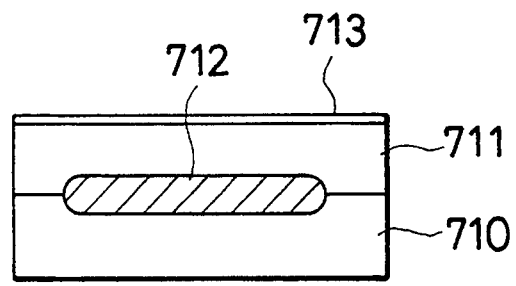
FIG. 7A through FIG. 7E are diagrams illustrating the fabrication process for a semiconductor device using the etching device and method of FIG. 1.

First, as shown in FIG. 7A, an imbedded layer 712 with a high concentration of impurities is formed in a silicon substrate 710 with a low concentration of impurities by diffusion.

On this upper layer another silicon layer 711 with a low concentration of impurities is formed by the epitaxial growth method, then an oxidized silicon film 713 is formed on the surface as a protective film.

Figure 7B:
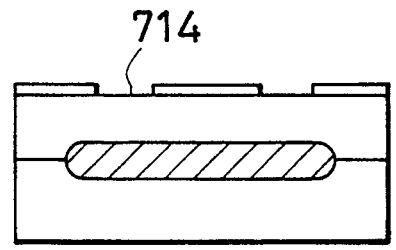

Then, as shown in FIG. 7B, an open section 714 is formed in the oxidized silicon film 713 by a photolithographic etching method.

Figure 7C:
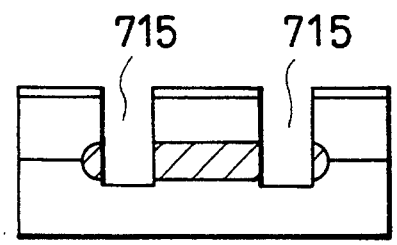

Next, as shown in FIG. 7C, a vertical groove 715 which is 30 to 50 μm wide is formed to penetrate the imbedded layer 712 using reactive ion etching, masking the oxidized silicon film 713.

Figure 7D:
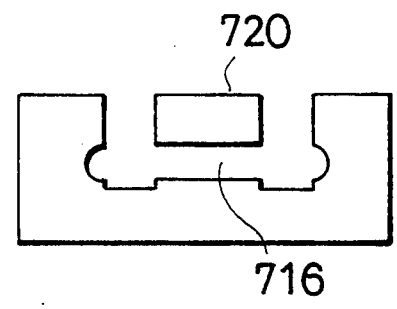

Following this, the silicon substrate is immersed in the etching tank of the etching device illustrated in FIG. 1 which is filled with the selective etchant of a 49 wt % fluoric acid, a 761 wt % nitric acid, and a 99.5% acetic acid (in the volumetric ratio of 1:3:8), and if the imbedded layer 712 is removed by selective etching, as shown in FIG. 7D, a cavity 716 is formed because of the difference in the concentration of impurities, and a 20 to 50 μm wide beam 20 is formed of single silicon crystals.

Figure 7E:
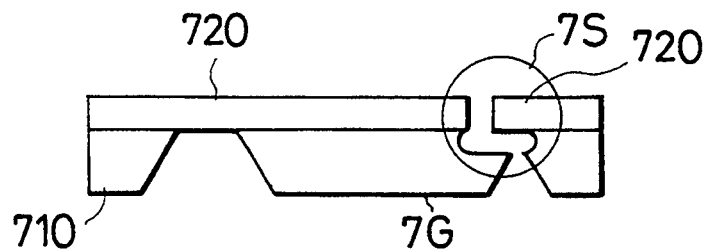

FIG. 7E is an example of a semiconductor acceleration sensor with a stopper in the acceleration detection direction. Using the present invention, a part of an overlapped section 7G is etched from the undersurface to reach a part of this cavity 716, so it is possible to form an etching stopper 7S very easily.

Using the above-mentioned monitoring device 1A shown in FIG. 1, a change in the nitrite ion concentration is detected by detecting a change in the concentration of NOx. A sodium nitrite solution is then added corresponding to the detected value obtained by the monitoring device 1A and the etching performed.

Here, while detecting the electric potential difference between the platinum electrode and the silicon electrode using an electron meter 101, the electric potential difference falls between certain specified values.

For example, when the electric potential difference is a specified value of 1.103 to 1.11 V, a specified amount of potassium nitrite is added to the etchant, and the electric potential difference becomes 1.103 V.

If etching is performed while this state is maintained, the electric potential difference is increased by decreasing the nitrite ions in the etchant. Here, with the electric potential difference at 1.11 V, when 2 ml (4 ml−2 ml=2 ml) of potassium nitrite is added, the electric potential difference becomes 1.103 V. By repeating this operation the electric potential difference can be maintained at a certain specified value, and the nitrite ion concentration can be adjusted to a specified concentration throughout the etchant.

In this manner, the concentration of the etchant can normally be maintained at a uniform value and etching control is simple.

The electric potential difference between the silicon electrode and the platinum electrode is measured in this manner, and sodium nitrite corresponding to this value is added and the nitrite ion is replenished or, $H_2O_2$ is added and by continued quenching of the nitrite ion, the reduced portion or the excess portion of the nitrite ion is replenished, and a uniform etching speed can be maintained.

A second embodiment of the present invention will now be explained referring to FIGS. 8 to 10.

In this second embodiment of the etching device, the explanation will be given for an etching method using the electric potential difference between a silicon electrode and a standard electrode to monitor the process.

Here, the explanation is given showing the monitoring device only; a device for adding nitrite solution drop-wise is left out for simplification.

Figure 8:
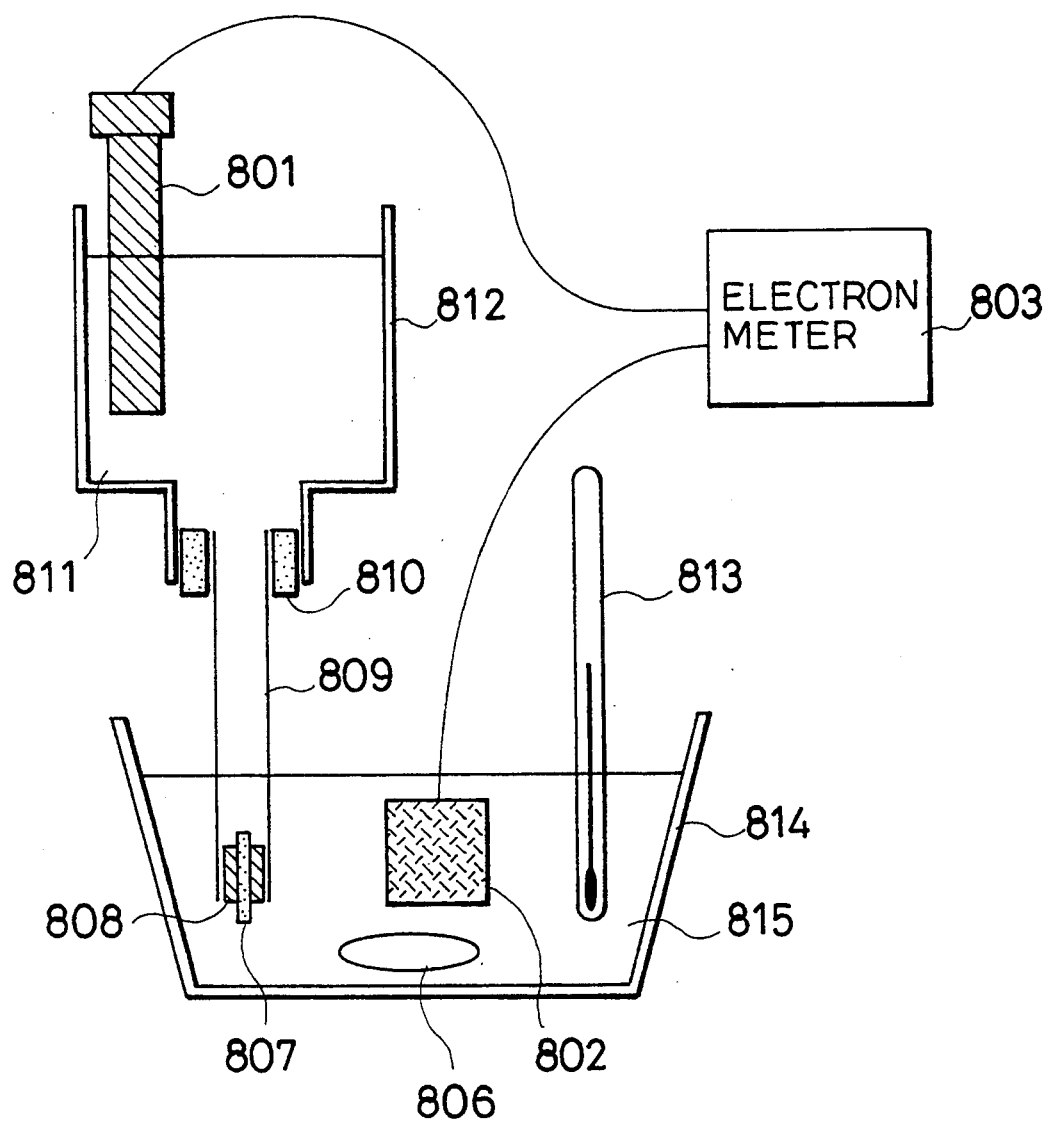
FIG. 8 is a diagram illustrating a second embodiment of an etching device of the present invention.

In this example, as illustrated in FIG. 8, to monitor the nitrite ion concentration in the etchant, the electric potential difference between a silicon electrode 802 and Ag/AgCl as a standard electrode 801 is measured.

In the standard electrode 801, a teflon tube 809 is connected through a silicon rubber connector 810 to the bottom surface of a polyethylene pipe 812 filled with a saturated KCl solution 811.

The tip of the teflon tube 809 is closed with a rod of porous alumina 807 and a fluororubber plug 808, and is electrically connected by means of the porous alumina rod 807 to an etchant 805 in a teflon beaker 804 as an etching tank.

The reference numeral 806 designates a stirring bar; the reference numeral 813, a thermometer; and the reference numeral 803, an electron meter for measuring the electric potential difference between the standard electrode 801 and the silicon electrode 802.

Here, 1.2 ml of a 49 wt% fluoric acid, a 61 wt% nitric acid, and a 99.5% acetic acid (in the volumetric ratio of 1:3:8) is used as an etchant. The output of the electron meter 803 when 1 ml at a time of a potassium nitrite solution (1 mol/lt) is added to this etchant, using a syringe, is shown in FIG. 9 and FIG. 10.

Figure 9:
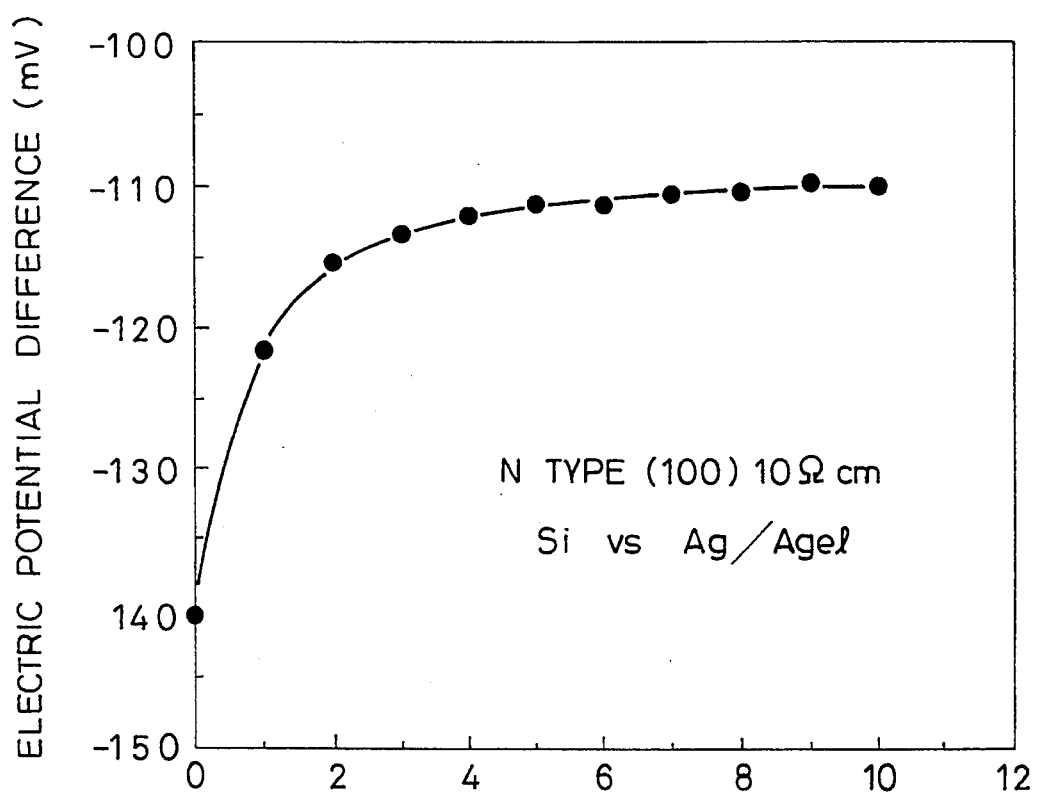
FIG. 9 is a graph showing the relationship between the electric potential difference and the amount of potassium nitrite solution added, using a silicon electrode (n type) and a standard electrode in the etching device shown in FIG. 8.
Figure 10:
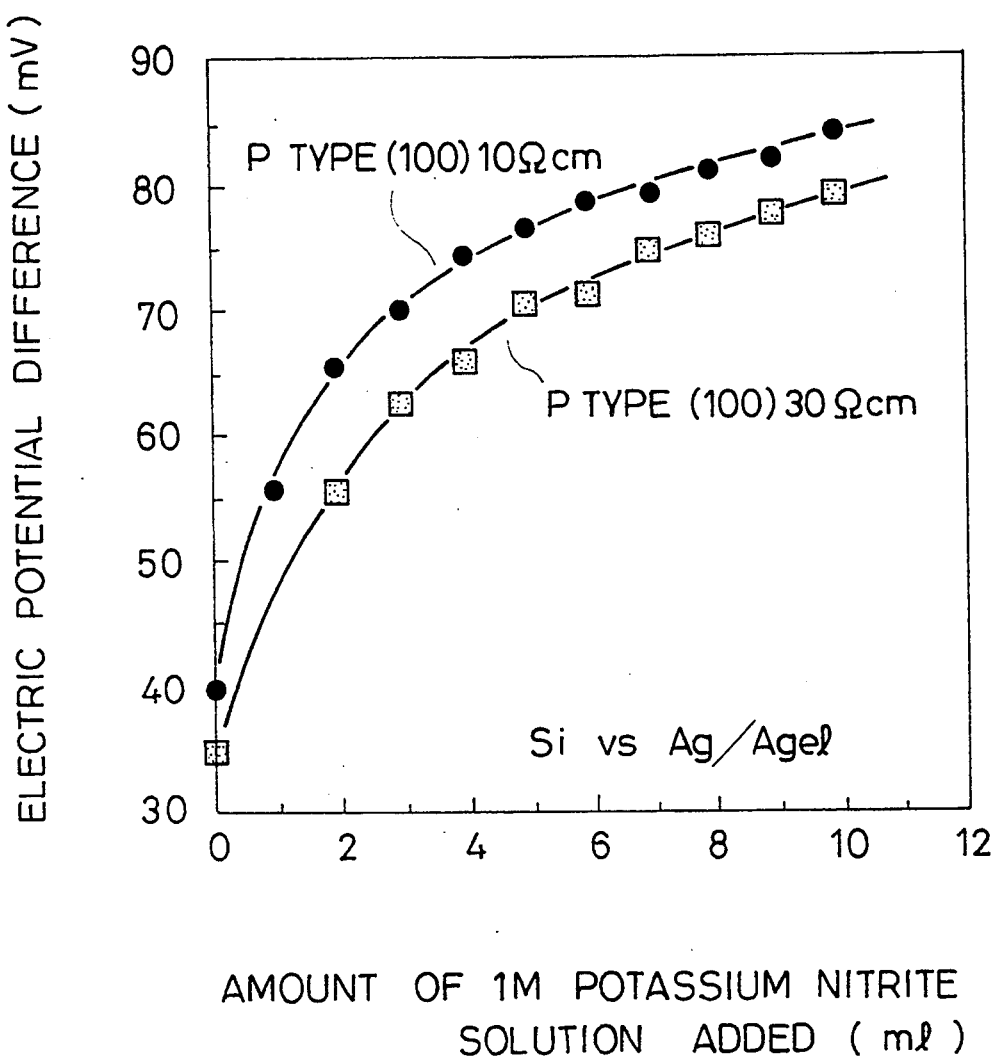
FIG. 10 is a graph showing the relationship between the electric potential difference and the amount of potassium nitrite solution added, using a silicon electrode (p type) and a standard electrode in the etching device shown in FIG. 8.

FIG. 9 shows the case where an n type silicon is used, and FIG. 10 shows the case where a p type silicon electrode is used.

No plateau region is seen in either case and the changes are smooth, indicating that this is a good process monitor.

In addition, when using this type of monitoring device the danger of contamination by heavy metals or the like is low, and the device can be used for a semiconductor process requiring clean conditions.

In addition, a porous alumina rod is used to fill the liquid in this embodiment, but if porous teflon is used, an even higher degree of cleanliness can be obtained. The standard electrode is not restricted to Ag/AgCl. Other materials may also be used.

In the first and second embodiments of the etching devices described above, in order to kept an optimum value of the concentration of the nitrite ions in the etchant the nitrite solution such as the potassium nitrite solution is added into the etchant.

This invention is not limited to the embodiments described above. For example, in order to kept the optimum value of the concentration of the nitrite ions in the etchant, it can be used for dissolving a silicon electrode under the control the voltage between the electrodes.

A third embodiment of an etching device 1100 according to the present invention will now be explained in detail, with reference to the drawings.

The etching device 1100 carry out the etching process with adding nitride ions under the control of the amount of a voltage applied between a silicon electrode 1108 and a opposing electrode 1109.

Figure 11:
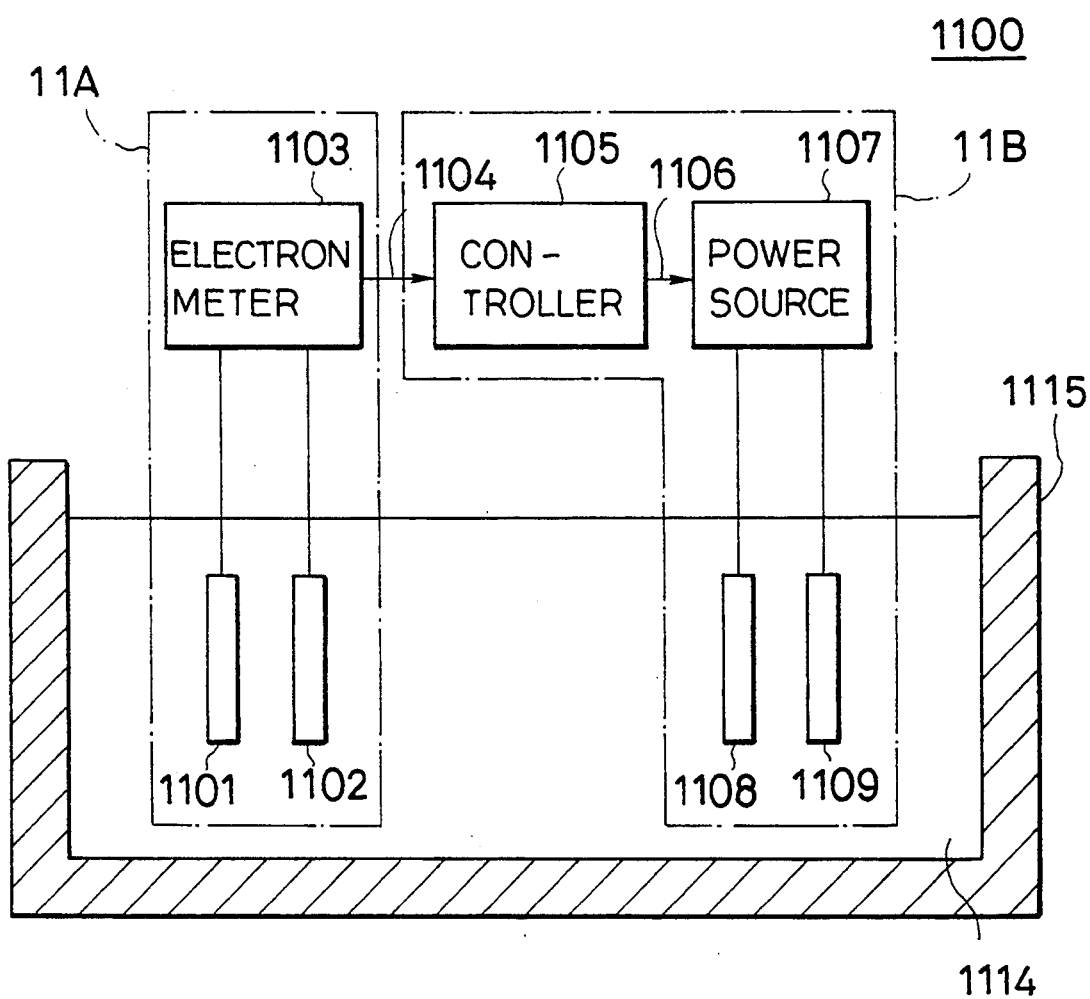
FIG. 11 is a diagram illustrating a third embodiment of an etching device of the present invention.

The etching device 1100 of the present invention, as illustrated in FIG. 11, has the special feature of comprising a monitoring device 11A which, in turn, comprises a platinum electrode 1101 and a carbon electrode 1102 immersed in an etching tank 1115 filled with an etchant 1114, and an etching control device 11B for controlling the voltage between a silicon electrode 1108 and an opposing electrode 1109 according to the results detected by the monitoring device 11A.

Using this etching device 1100, etching is performed while adding nitrite ions by controlling the voltage applied between the silicon electrode 1108 and the opposing electrode 1109 so that the nitrite ion concentration is normally maintained at a desired value.

The monitoring device 11A detects changes in the nitrite ion concentration in the etching tank 1115 by detecting the NOx concentration in the tank as an electric potential difference between the platinum electrode 1101 and the carbon electrode 1102.

When a drop in the nitrite ion concentration is detected by the monitoring device 11A, a controller 1105 of the etching control device 11B transmits a control signal 1106 to a power source 1107 to control the electric potential difference between the silicon electrode 1108 and the opposing electrode 1109.

Specifically, when a drop in the nitrite ion concentration of the etchant 1114 is detected by the monitoring device 11A, the controller 1105 controls a power source 1107 so that a bias is applied to the silicon electrode 1108 and the silicon electrode is dissolved.

Nitrite ions generated by the dissolution reaction of the silicon electrode 1108 replenish the etchant. Then, when an optimum value for the nitrite ion concentration of the etchant 1114 is detected by the monitoring, the controller 805 controls the power source 1107 to apply a bias to the silicon electrode 1108 to the extant 1114 that dissolution is not produced, so that the replenishment of the nitrite ions is halted.

Next, a process for forming a beam section for a pressure sensor will be explained for the selective etching of a silicon substrate, using this etching device.

Figure 12A:
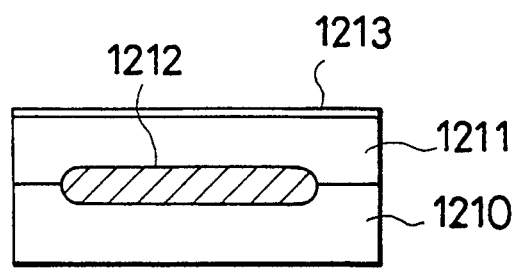
FIG. 12A through FIG. 12E are diagrams illustrating a fabricating process for a semiconductor device used in an etching method of the etching device shown in FIG. 11.

First, as shown in FIG. 12A, an imbedded layer 1212 with a high concentration of impurities is formed by diffusion in a silicon substrate 1210 with a low concentration of impurities. On another silicon layer 1211 with a low concentration of impurities is formed on this upper layer using the epitaxial growth method, then an oxidized silicon film 1213 is formed on the surface as a protective film.

Figure 12B:
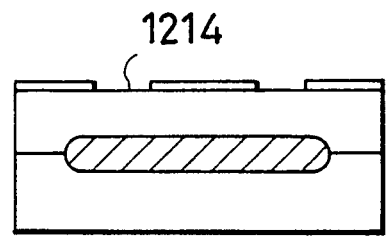

Then, as shown in FIG. 12B, an open section 1214 is formed in the oxidized silicon film 1213 by a photolithgraphic etching method.

Figure 12C:
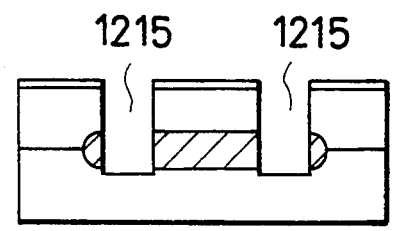

Next, as shown in FIG. 12C, a vertical groove 1215 which is 30 to 50 μm wide is formed by reactive ion etching to penetrate the imbedded layer 1212 to mask the oxidized silicon film 1213. The silicon substrate is then immersed in the etching tank 1115 of the etching device 1100 illustrated in FIG. 11 which is filled with the selective etchant of a 49 wt% fluoric acid, a 61 wt% nitric acid, and a 99.54 acetic acid (in the volumetric ratio of 1:3:8).

Figure 12D:
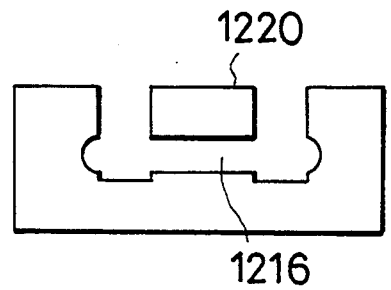

When the imbedded layer 1112 is removed by selective etching, as shown in FIG. 12D, a cavity 1216 is formed because of the difference in the concentration of impurities, and a 20 to 50 μm wide beam 1220 is formed of single silicon crystals.

In this process, a change in the nitrite ion concentration is detected by detecting a change in the NOx concentration, using the monitoring device AA, the voltage applied to the silicon electrode is controlled according to this detected value, and etching is carried out.

In this manner, by applying a bias voltage to the silicon electrode so that silicon is dissolved in the etchant to continuously replenish the nitrite ions, the drop in nitrite ions is corrected and a uniform etching rate can be maintained.

Figure 12E:
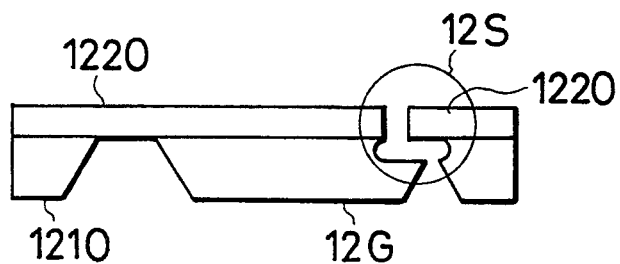

FIG. 12E is an example of a semiconductor acceleration sensor with a stopper in the acceleration detection direction.

Using the embodiment according to the present invention, a portion of an overlapped section 12G is etched from the undersurface to reach a section of this cavity 1216, so it is possible to form an etching stopper 12S very easily.

The example was given in which two electrodes are used, the silicon electrode 1108 and the opposing electrode 1109, but it is also possible to use three electrodes by adding a reference electrode (standard electrode). The control function can be further improved by using the power source as a potentiostat.

In addition, the material for the opposing electrode is not restricted to platinum. Another chemically stable material such as carbon may be used.

In the above-described third embodiment the dissolution of the silicon electrode is controlled using ON-/OFF control.

However, the application of a bias voltage may also be used to control the promotion of the dissolution reaction of the silicon electrode as the nitrite ion concentration increasingly deviates from the optimum value.

A fourth embodiment of the present invention will now be explained. This example, as illustrated in FIG. 13, has the feature that the same silicon electrode is used for monitoring the nitrite concentration of the etchant and for replenishing the nitrite ion by the dissolution reaction.

Figure 13:
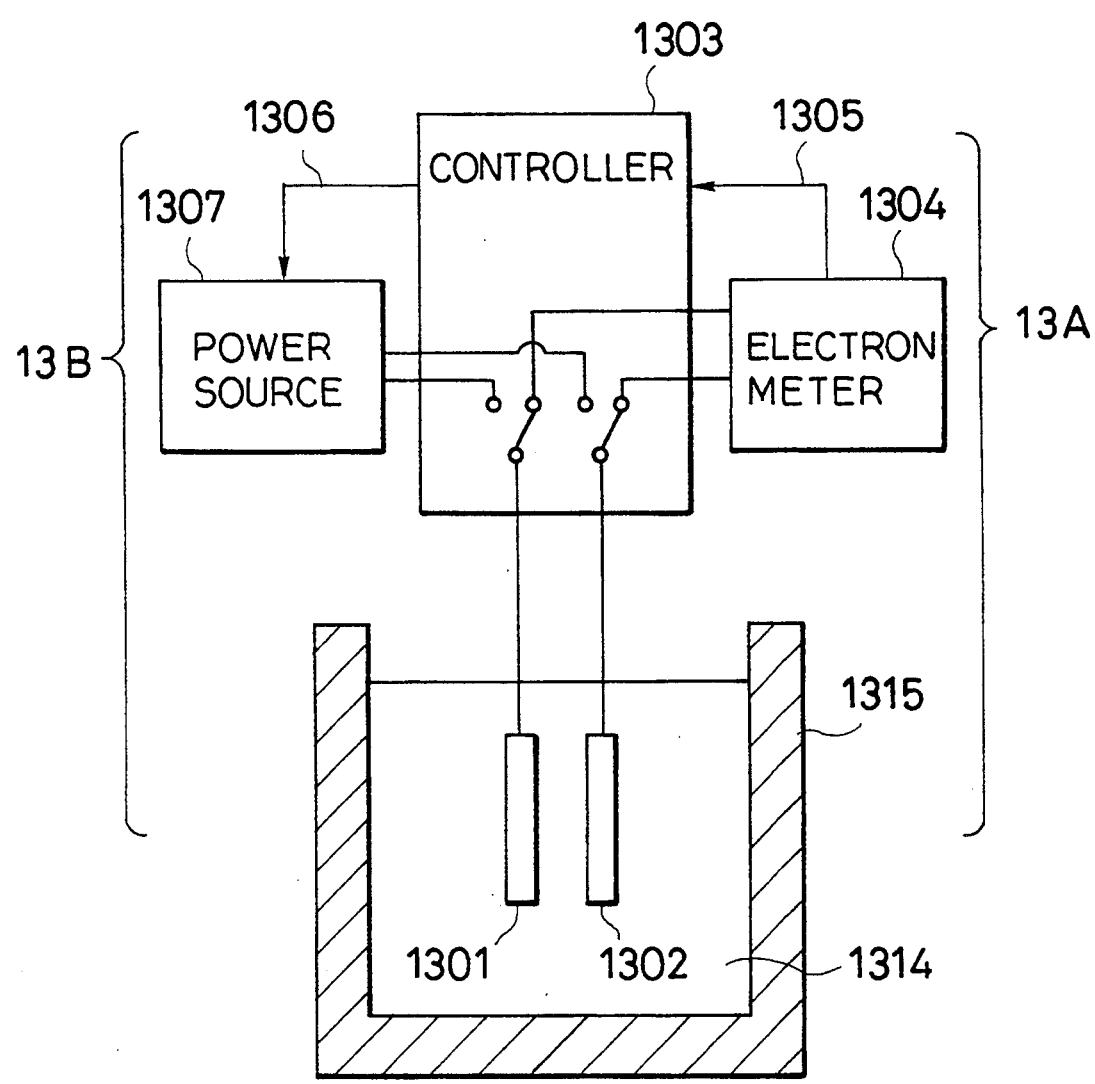
FIG. 13 is a diagram illustrating a fourth embodiment of an etching device of the present invention.

Specifically, this etching device, as shown in FIG. 13, has the special feature of being provided with a monitoring device 13A, comprising a silicon electrode 1301 and a platinum electrode 1302 immersed in the etching tank 1315 filled with the etchant 1314 with both electrodes connected to an electron meter 1304; and an etching control device 13B for controlling the voltage between the silicon electrode 1301 and the opposing electrode 1302, by controlling the voltage of a powers source 1307 based on the output of a controller 1303.

Using this device, etching is performed while adding nitrite ions by controlling the voltage applied between the silicon electrode 1301 and the platinum electrode 1302 so that the nitrite ion concentration is normally maintained at a desired value.

The monitoring device 13A detects changes in the nitrite ion concentration in the etching tank 1315 by detecting the NOx concentration in the tank as an electric potential difference between the silicon electrode 1301 and the platinum electrode 1302.

When a drop in the nitrite ion concentration is detected by the monitoring device 13A, the controller 1303 of the etching control device 13B transmits a control signal 1306 to the power source 1307 to control the electric potential between the silicon electrode 1301 and the platinum electrode 1302.

Specifically, when a drop in the nitrite ion concentration of the etchant is detected by the monitoring device 13A, the silicon electrode 1301 and the platinum electrode 1302 are connected to the power source 1307. The controller 1303 then controls the power source 1307 so that a bias is applied to the silicon electrode 1301 and the silicon electrode is dissolved. The etchant is replenished with nitrite ions formed by the dissolution reaction of the silicon electrode 1301. The nitrite ion concentration in the etchant is then adjusted to the optimum level.

Once again the silicon electrode 1301 and the platinum electrode 1302 are connected to the electron meter 1304 and the monitoring device 13A is reactivated. When the nitrite ion concentration drops below the optimum value these electrodes are again connected to the power source.

Excellent control is obtained by repeating this operation, so that stable, continuous etching is possible. In this example, it is possible to use a simple configuration wherein a single electrode serves as a monitoring electrode and a control electrode.

The two-electrode method is used in the above-mentioned fourth embodiment, but a third electrode can be added as a reference electrode.

The control function can be further improved by using the power source as a potentiostat.

The material for the opposing electrode is not restricted to platinum.

Another chemically stable material such as carbon may be used.

A fifth embodiment of a etching device according to the present invention will now be explained.

Figure 14:
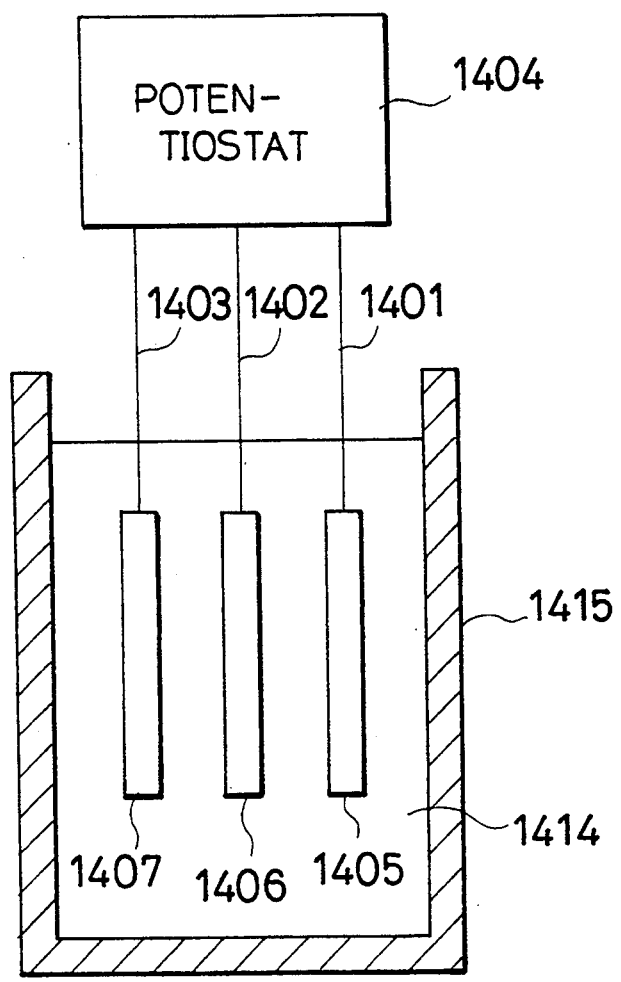
FIG. 14 is a diagram illustrating a fifth embodiment of an etching device of the present invention.

In this example a potentiostat 1404 is used, as shown in FIG. 14. A silicon electrode 1405 is connected to an operating electrode terminal 1401 on the potentiostat 1404; a platinum electrode 1406 is connected to an opposing electrode terminal 1402; and a platinum electrode 1407 is connected to a reference electrode terminal 1403. The potentiostat 1404 applies a voltage between the silicon electrode 1405 and the platinum electrode 1407 so that the electric potential difference between the silicon electrode 1405 and the platinum electrode 1407 reaches a certain set value.

As a result, the amount of the dissolution reaction of the silicon electrode 1405 is controlled, and, accordingly, the nitrite ion concentration in the etchant is controlled to a predetermined value of the set potential of the potentiostat.

In the fifth embodiment, the material for electrode 1406 as an opposing electrode for electrolysis of the silicon electrode 1405 is not limited to platinum.

Another chemically stable material such as carbon may be used.

In addition, the platinum electrode 1307 may be combined with the silicon electrode 1305 to function as a process monitor. Also, another noble metal, other than platinum, or a carbon electrode or the like may be used.

These embodiments have been explained for the case where a mixture of fluoric, nitric, and acetic acid was used.

However, the present invention may also be applied where fluoric acid and nitric acid are the main ingredients.

As clearly explained above, in the third to fifth embodiments according to the present invention a stable etching process can be continuously performed by the dissolution of nitrite ions, or the dissolution of a silicon electrode to form nitrite ions in the processing liquid.

Using the configurations of the etching devices of the above-mentioned third to fifth embodiments, the change in the nitrite ion concentration is monitored by the electric potential difference between the monitor electrodes. According to the result of this monitoring, compensation is made for the change in the nitrite ion concentration as the etching proceeds by controlling the voltage applied to a semiconductor electrode of silicon or the like. T The semiconductor of silicon or the like dissolves in the etchant, and because nitrite ions are generated by a reaction with this silicon, a uniform nitrite concentration is normally maintained so that good etching characteristics can be maintained.

In the foregoing first to fifth embodiments, the electric potential difference between the two electrodes, for example the silicon electrode and the platinum electrode, is used as a method of monitoring the nitrite ion concentration in the etchant, but, the present invention is not limited to the method.

Other methods such as a method of monitoring the absorption of the etchant, a method of monitoring the electric potential of the silicon electrode immersed in the etchant, or a method of monitoring the changes of the NOx concentration in the gas vapor which is the gas-liquid equilibrium with the etchant (Japanese Patent Application 3-261951) and the like may also be used.

The following method can be given as a method of monitoring the absorption.

For example, as in the etching process used above, 1 ml of a nitrite solution (1 mol/liter) is added to 100 ml of the selective etchant of a 49 wt% fluoric acid, a 61 wt% nitric acid, and a 99.54% acetic acid (in the volumetric ratio of 1:3:8), then a 1 ml sample is taken out immediately after the addition, one hour after, two hours after, and three hours after, and analyzed using the color comparison method.

This analysis shows that the nitrite ions are reduced to one-half after about 40 minutes, and at 2 to 3 hours almost all the nitrite ions have disappeared.

Accordingly, in order to provide a uniform concentration of nitrite ions introduced into the etchant, it is necessary to continuously replenish the reduced amount during the selective etching process, normally by adding nitrite solution.

Other methods which can be used for detecting the NOx concentration include electrochemical methods such as the low potential electrolysis method; optical methods such as the infrared absorption method, the visible light absorption photometric method, the light interference method, the chemical luminescence method, and the like; and electrical methods such as the semiconductor method and the like. Also, two or more detection devices, or two or more types of detection devices may be used for monitoring NO and NO2 separately.

A sixth embodiment of the present invention will now be explained.

Figure 15:
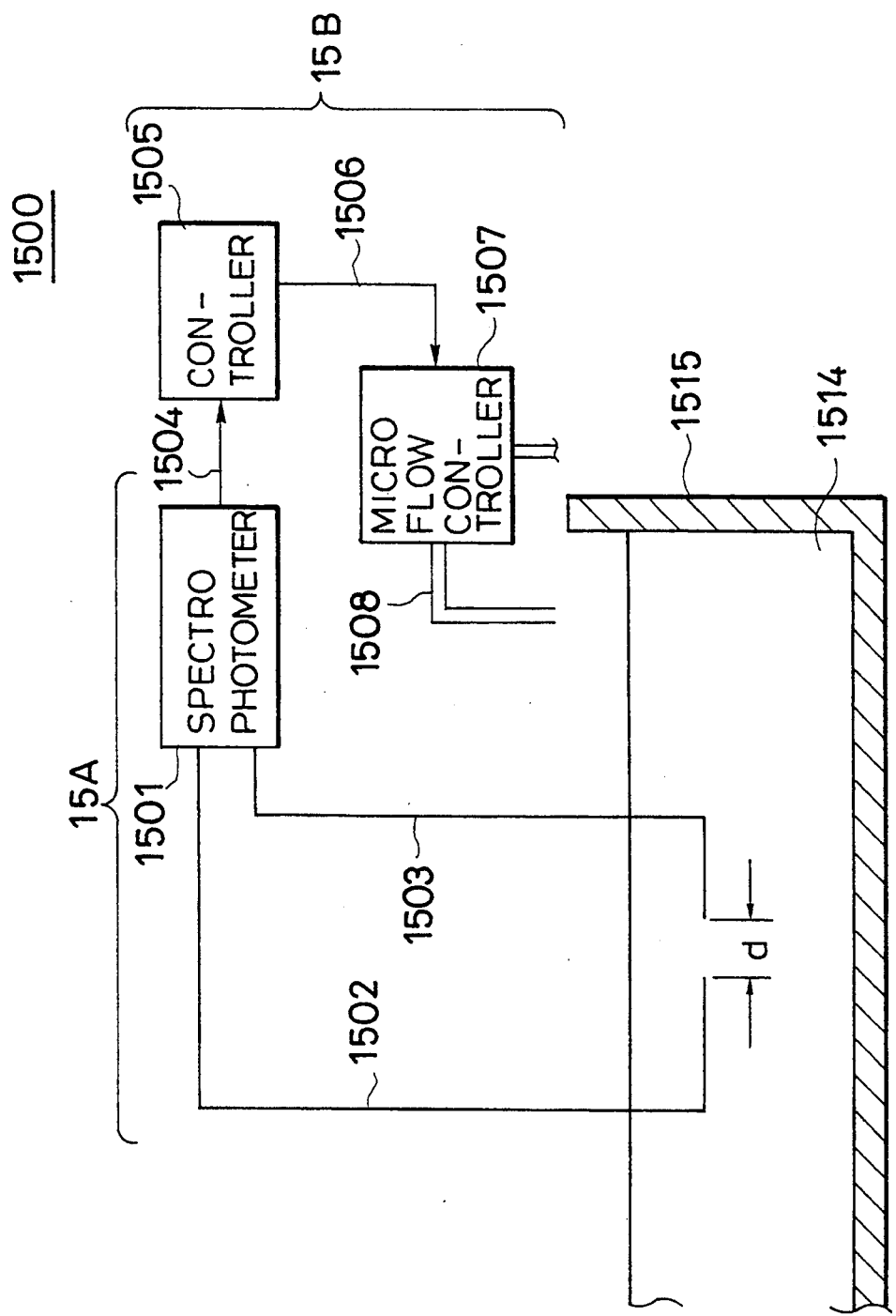
FIG. 15 is a diagram illustrating a sixth embodiment of an etching device of the present invention.

This etching devices 1500 of the sixth embodiment, as shown in FIG. 15, monitors the nitrite ion concentration in the etchant by absorption.

The tips of a light-projecting fiber 1502 and a light-receiving fiber 1503 separated by a space d are immersed in the etching tank 1515 filled with the etchant 1514.

A monitoring device 15A which is a spectrophotometer 1501 connected to the other ends of these fibers, and an etching control device 15B for adding a nitrite salt corresponding to the results of the monitoring, are mounted on the etching device 1500 which has the special feature of etching while a nitrite salt solution is added so that the nitrite ion concentration is maintained at a normally desired value.

The monitoring device 15A detects the changes in the nitrite ion concentration in the etching tank 1515 by detecting the NOx concentration in the etching tank 1515 as the electrical potential difference between the light-projecting fiber 1502 and the light-receiving fiber 1503 as a degree of absorption, using the spectrophotometer 1501.

When a drop in the nitrite ion concentration is detected by the monitoring device 15A, a signal 1504 is transmitted, and the controller 1505 of the etching control device 15B transmits a control signal 1506 to the micro-flow controller 1507 to cause the nitrite salt solution to be added into the etching tank 1515 through a nozzle 1508.

Specifically, when a drop in the nitrite ion concentration in the etchant 1514 is detected by the monitoring device 15A, the controller 1505 controls the micro-flow controller 1507, and when the nitrite salt solution is added, the nitrate ions throughout the etchant are replenished. Then, the fact that the nitrite ion concentration in the etchant has reached an optimum value is detected by the above-mentioned monitoring and the controller 1505 controls the micro-flow controller 1507 so that the replenishment of the nitrite ion is halted.

Figure 16:
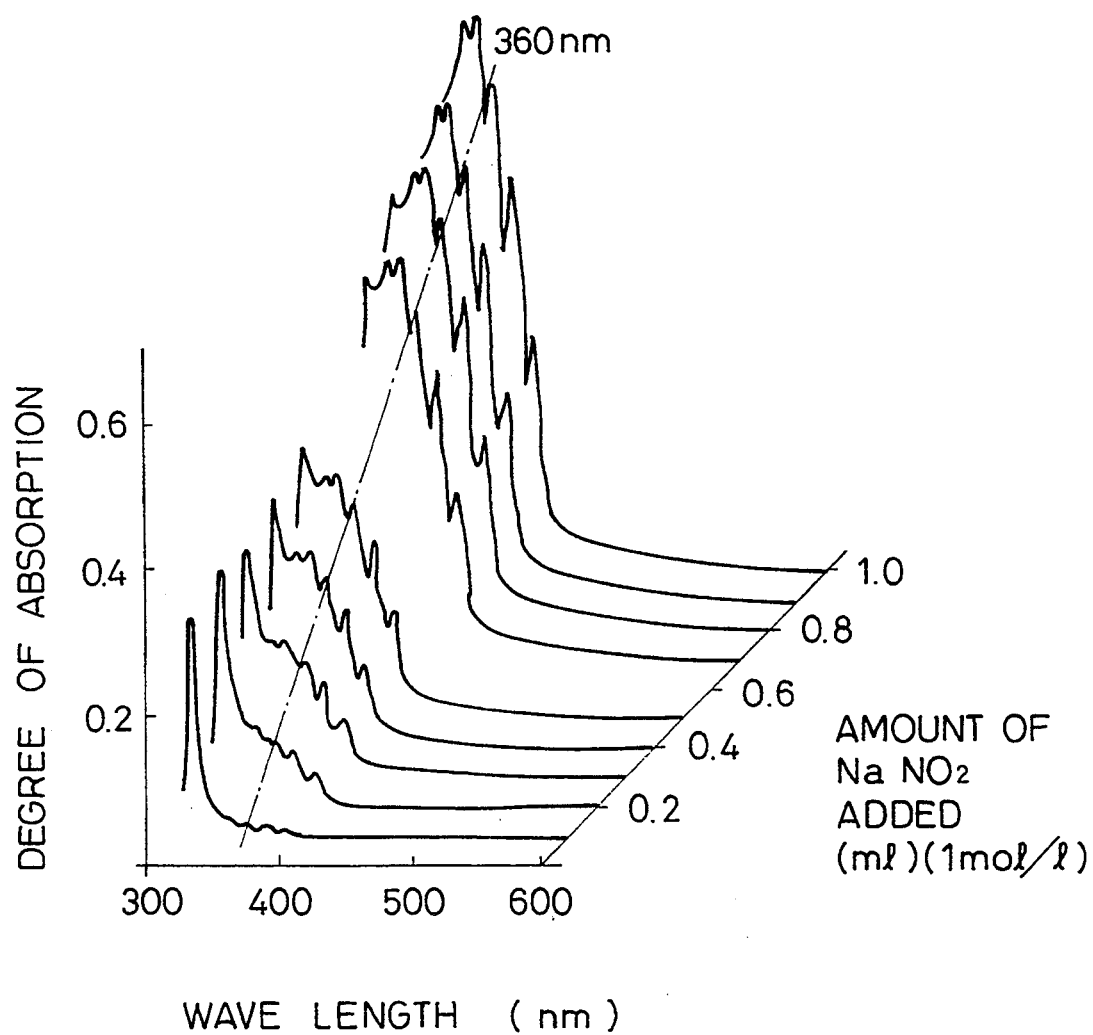
FIG. 16 is a graph showing the relationship between the degree of absorption and the amount of sodium nitrite added.

Next, the results of measuring the relationship between the degree of absorption and the amount of sodium nitrite added to the etchant 1514 are shown in FIG. 16. The results of measuring the relationship between the degree of absorption and the nitrite ion concentration are also shown in FIG. 16.

As clearly shown in this graph, there is no plateau region and the changes are smooth, indicating that this is a very superior monitor. Here also, 100 ml of a 49 wt% fluoric acid, a 61 wt% nitric acid, and a 99.5% acetic acid (in the volumetric ratio of 1:3:8) is used as the etchant, is added to each of a series of teflon beakers.

A sodium nitrite solution (1 mol/lt) is added in 0.1 to 1.0 ml stages to the teflon beakers, and after agitating for less than 60 seconds, samples are placed in a polystyrene optical absorption cell (optical path length 1 cm) and the spectrum is measured by wave length scanning using the spectrophotometer, the measurement being made within three minutes.

Figure 17:
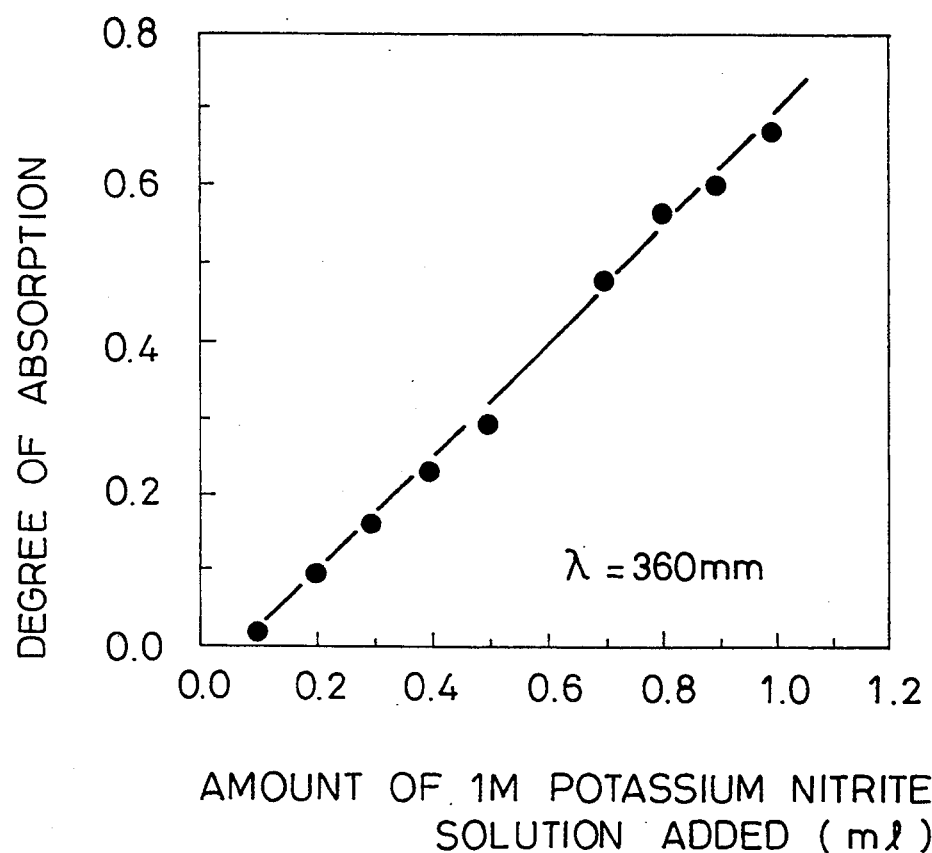
FIG. 17 is a graph showing the relationship between the degree of absorption and the amount of potassium nitrite added.

In this manner, the output of the electron meter 1503 when the addition is made using a syringe is shown in FIG. 17. This graph shows the relationship between the degree of absorption at a wave length of 360 nm, believed to be the absorption peak for the nitrite ion, and the amount of 1M potassium nitrite solution added.

In this manner, even when the monitor wave length is fixed, the nitrite ion concentration continues to increase linearly, and the degree of absorption is also seen to increase linearly.

Thus, it is possible to monitor the etchant characteristics by measuring the degree of absorption of the etchant. Because the response is shown to be linear, it is seen that highly precise monitoring characteristics can be obtained under optional process conditions, not only those close to optimum conditions.

In this sixth embodiment the light-projecting and light-receiving fibers are positioned in opposition, but it is possible to make an intelligent sensing head by combining a prism, lens and the like.

Figure 18:
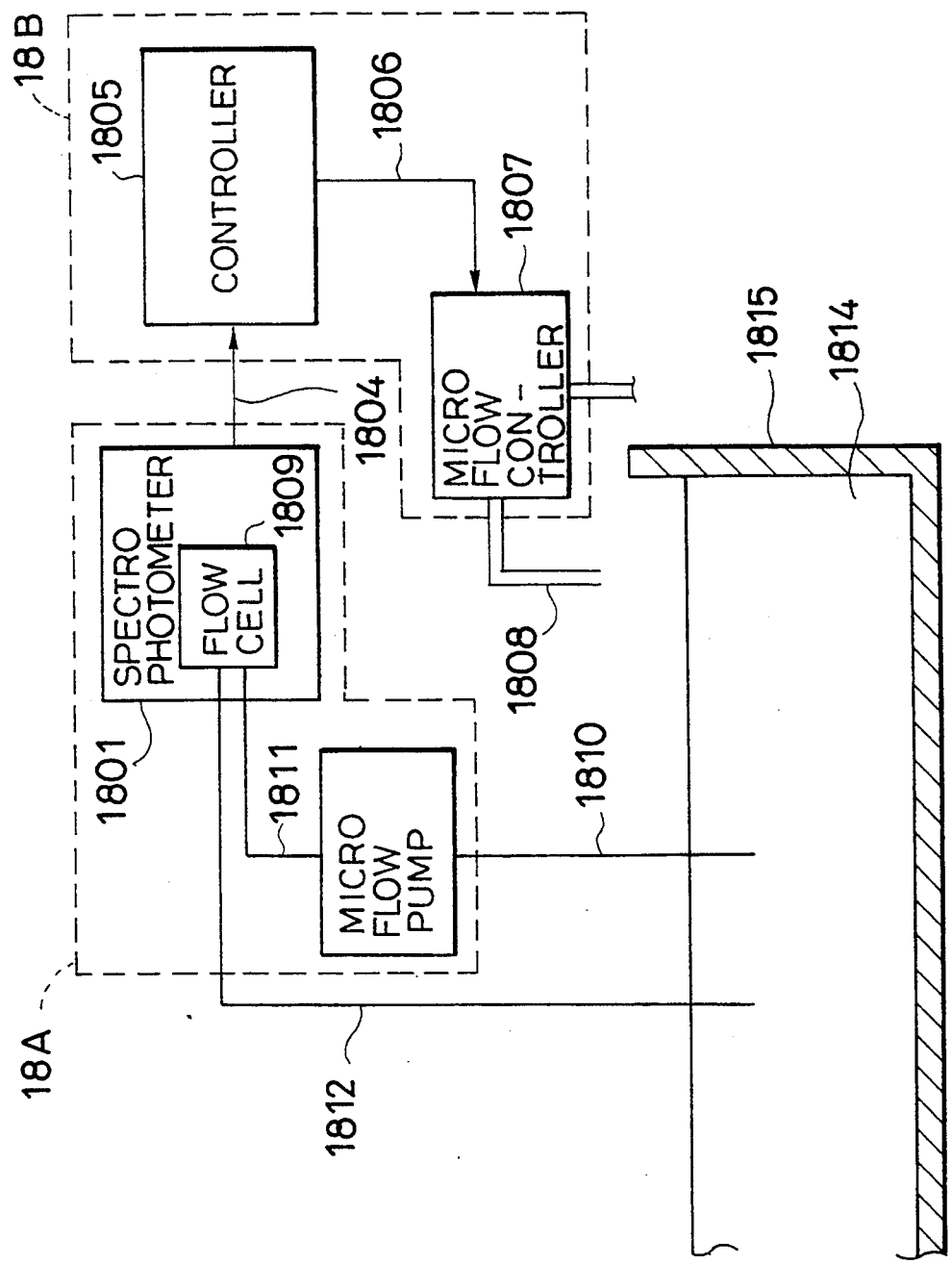
FIG. 18 is a diagram illustrating a seventh embodiment of an etching device of the present invention.

Also, in this sixth embodiment the degree of absorption in the etching tank 1515 is sensed, but, as shown in a seventh embodiment in FIG. 18, the etchant 1814 may also be sensed by a spectrophotometer 1801.

With this method, the etchant 1814 is pumped up by the indicator pump (or a micro flow pump) through a tube 1810 and introduced into a flow cell 1809 inside the spectrophotometer 1801, then once again is returned to the etching tank through the tube 1811.

The signal 1804 for the degree of absorption of the etchant in the flow cell 1809 is generated in the controller 1805 of the etching control device 18B.

In this manner, when a drop in the nitrite ion concentration is detected by the monitoring device 18A, the signal 1804 is transmitted, and the controller 1805 of the etching control device 18B transmits the control signal 1806 to the micro-flow controller 1807 so that the nitrite solution is added to the etching tank 1815 through a nozzle 1808.

Specifically, when a drop in the nitrite ion concentration of the etchant is detected by the monitoring device 18A, the controller 1805 controls the micro-flow controller 1807 so that the nitrite solution is added.

Then, when the nitrite solution is added, the nitrite ion in the etchant is replenished. When the monitor determines that the nitrite ion concentration in the etchant has reached an optimum value, the controller 1805 controls the micro-flow controller 1807 so that the replenishment of the nitrite ion is halted.

A spectrophotometer is used in the above-described sixth and seventh embodiments, but the same type of system comprising a light source capable of generating a beam of close to 360 nm and a detector capable of receiving such a light beam is also acceptable.

The absorption of a single wave length may also be monitored using a filter or the like.

Also, all these embodiments were explained for the case where a mixture of fluoric, nitric, and acetic acid was used. However, the present invention may also be applied where fluoric acid and nitric acid are the main ingredients.

As clearly explained above, in the present invention the nitrite ion concentration is monitored by detecting the electric potential difference between a semiconductor electrode and an opposing electrode or by measuring the degree of absorption of the etchant, then, according to the results of this monitoring, a stable etching process can be continuously performed by adding a nitrite salt to the etchant during etching.

Using the above first to fifth embodiments, changes in nitrite ion concentration are monitored by the electric potential difference and the like between a pair of monitoring electrodes made up of a semiconductor electrode of silicon or the like and an opposing electrode which is resistant to etching. According to the result of this monitoring, compensation is made for the change in the nitrite ion concentration as the etching proceeds by adding a chemical which generates the necessary quantity of nitrite ions, or a chemical which quenches nitrite ions, for example, a hydrogen peroxide solution or the like or by applying a predetermined voltage to a semiconductor electrode. The etchant therefore is normally maintained in a stable condition.

By means of the above sixth and seventh embodiments, the degree of absorption of the processing liquid is detected and changes in nitrite ion concentration are monitored by this absorption. According to the result of this monitoring, compensation is made for the change in the nitrite ion concentration as the etching proceeds by adding a chemical which generates the necessary quantity of nitrite ions, or a chemical which quenches nitrite ions, for example, hydrogen peroxide solution or the like. The etchant therefore is normally maintained in a stable condition.

The mechanism of an isotropic selective etching reaction has not as yet been fully explained, but the change in concentration of the nitrite ion concentration $dC/dt$ can be approximated by Equation (1).

$$dC/dt = k_1 C_0 + k_2 C - k_3 C \quad (1)$$

The first term on the right side of Equation (1) represents the rate of formation of nitrite ions generated by the oxidation of silicon by nitric acid ions. $C_0$ is the concentration of nitric acid, and because a large volume exists as bulk throughout the etchant, this may be considered as uniform.

$k_1$ is a parameter constant which includes the device parameters related to the type of agitation, the temperature setting, and the like, for a device for a selective etching process; parameters for a semiconductor device manufactured for selective etching, specifically parameters related to the volume and concentration of impurities in the part to be etched, and the shape; and a series of parameters such as a constant for the rate of whole infusion of nitric acid ions into the silicon, and the like.

The second term on the right side of the equation represents the rate of formation of nitrite ions, generated autocatalytically by the oxidation of silicon by nitrite ions (or a nitrogen compound with a low oxidation number). C is the nitrite ion concentration, and is a readily-changeable variable. $k_2$ is a parameter constant similar to $k_1$, related to the nitrite ion.

The third term on the right side of the equation represents the rate of disappearance of the nitrite ion which is decomposed with the formation of gas by the acidity of the etchant. $k_3$ is a parameter constant containing a device parameter and a series of parameters relating to a constant for the decomposition rate of the nitrite ions or a gas-liquid distribution factor for gas generated by this decomposition.

In the case where the selective etchant is a virgin solution, C=0 and the second and third terms can be ignored. Accordingly, when the etchant is almost a virgin solution, the first term becomes dominant. However, the first term is not a very large value when C=0, because most of the etching cannot be monitored.

In the first term, if the nitrite ion concentration gradually increases, the second term increases, and, accordingly, the third term, keeping pace, becomes a large value. If the maximum nitrite ion concentration in the selective etching process is $C_s$ (a constant determined from a parameter for a manufactured semiconductor device and a device parameter and the like), $k_1 C_0 < k_2 C_s$, therefore the first term may be ignored. Supposing that at t=0, $C=C_s$, then the type of subsequent reaction system is specified under either of the following conditions.

$$k_2 > k_3 \text{(in detail, } k_1 C_0 + k_2 C_s > k_3 C_s\text{)} \quad (2)$$

$$k_2 > k_3 \text{(in detail, } k_1C_0 + k_2C_s < k_3C_s\text{)} \quad (3).$$

In the case of (2), the nitrite ion concentration is increased exponentially. This means that the etching rate is out of control.

In the case of (3), the nitrite ion concentration is decreased exponentially, which means that the etching reaction almost stops.

Conventionally, selective etching is said to proceed autocatalytically and the nitrite ions must be removed by some method. This indicates that the conditions of (2) are present. In short, the method invented by Muraoka et al. is a control method for a reaction system with the conditions of (2), and is a method by which an excess of nitrite ions generated is removed in succession by oxiding the nitric acid ions with hydrogen peroxide solution. Naturally, the effect of the third term in Equation (1) is cancelled by the effect of the second term.

However, an isotropic selective etching process normally does not proceed under the conditions of (2) above. For example, even when the device parameters are fixed by the parameters of the manufactured semiconductor device, the relationship of the above parameter constants $k_2$, $k_3$ is probably as shown in (3).

Conventionally, an isotropic selective etching process is provided in an IMPAT manufacturing process and silicon substrate wrapping or the like. However, the isotropic selective etching process invented by the present inventors is applicable to a micromachining process represented by a fabricating process for an intelligent sensor, and, together with the progress in miniaturization of the circuits, the volume of the parts to be etched also becomes one over several ten thousandths as compared with the case of the IMPAT manufacturing process and the like.

From the large disparity in parameters for a manufactured semiconductor device, the parameter constants $k_2$, $k_3$, are extremely small compared with the conventional parameters.

Accordingly, the relationship of the parameter constants $k_2$, $k_3$ is as shown in (3), and a reaction system is formed in which the third term in Equation (1) cannot be ignored.

Under conditions of this type for the isotropic selective etching process, a successive supply of nitrite ions which are decomposed with gas formation must be continued to maintain the nitrite ion concentration at the optimum. If this feed rate is taken as A and added as supply term to Equation (1), Equation (2) is obtained, as follows.

$$dC/dt = k_1C_0 + k_2C - k_3C_s + A \quad (4).$$

In Equation (4), if C is maintained uniform, then $dC/dt = 0$. Accordingly, if $dC/dt = 0$ is put into Equation (4), then $$A = k_3C_s - k_1C_0 - k_2C_s \quad (5)$$

Accordingly, while measuring the nitrite ion concentration, even when not starting titration, for example, first, a control method is possible by which 0.5 ml of 1M potassium nitrite solution is added at a time.

Figure 19:
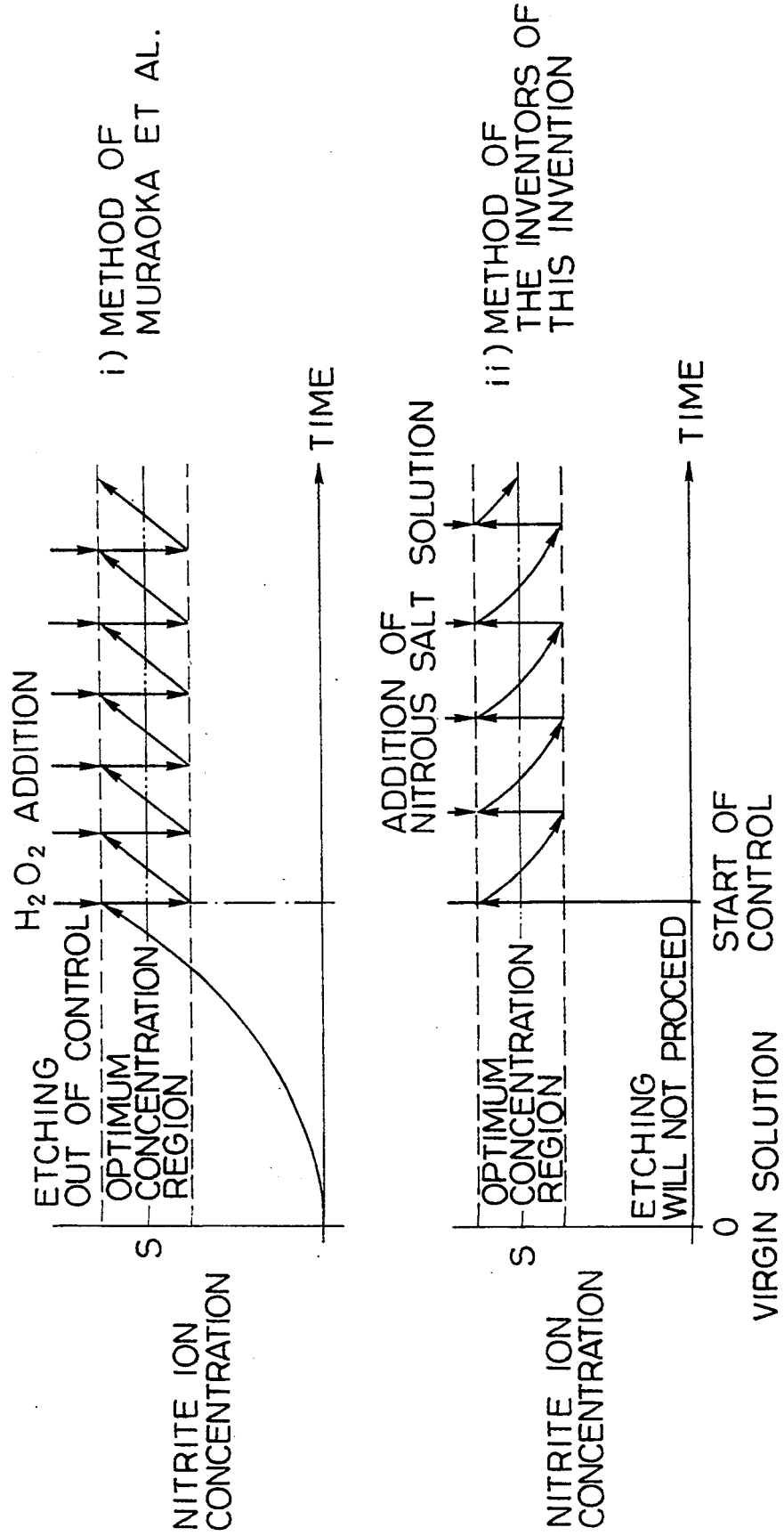
FIG. 19 is a chart comparing the change in nitrite ion concentration with time for the method of Muraoka et al and the method of the present invention.

FIG. 19 gives a comparison between the method of Muraoka et al. and the method of the inventors of the present invention. When $k_2$ and $k_3$ are almost the same, the nitrite ion concentration need not be controlled, but in practice, both $k_2$ and $k_3$ change as the etching process proceeds (normally become smaller), therefore control is necessary.

In the foregoing explanation, the order of reaction is taken as "1" excepting the case in which a "0" order is not occurred, the explanation remains essentially the same as above.

In addition, even under the conditions in (2), in practice the nitrite ion concentration does not continue to increase exponentially, and it is only natural that the reaction, which is a chemical transport rate-determining reaction, reaches a peak.

This is a condition in which the nitrite ion concentration deviates considerably from the optimum concentration so no great modification of the foregoing explanation is required.

As explained above, it is possible to control an isotropic selective etching process under the condition (3), not only by directly adding nitrite ions from the nitrite acid solution but also by using chemicals, for example, various types of metals or silicon itself, which generate nitrite ions by reacting with the etchant.

It is also possible to add a mixture of fluoric acid and nitric acid, known as 'used solution' which carries out a fusion reaction with large quantities of silicon. In addition, it is possible to pass a current through nitrogen dioxide to generate nitrite ions by ionization equilibrium.

Among the control methods explained above, the methods of adding of a silicon leaf, passing a current through nitrogen dioxide, adding a nitrite acid solution, and adding used solution, can be used in a process for fabricating devices such as a bipolar transistor and CMOS by three-dimensional machining using selective etching, in comparison with the method of using nitrite acid, because the control method does not include alkali metals (such as Na, K and the like), and a process which has the problem of contamination by alkali metals, for example, such as hollowing out SOI.

Of course, there is no such restriction with a normal intelligent sensor process, because the circuits are fabricated by three-dimensional machining.

What is claimed is:

1. An etching device performing an etching process on a material immersed in a processing liquid, using a processing liquid comprising a mixture of acids selected from the group consisting of fluoric acid, nitric acid, and acetic acid to produce a processing liquid further comprising nitrite ions formed as the result of a dissolution reaction between said material and said processing liquid, the etching device comprising:
   a semiconductor electrode immersed in the processing liquid;
   an opposing electrode which is also immersed in the processing liquid, opposing said semiconductor electrode;
   means for detecting an electric potential difference between said semiconductor electrode and said opposing electrode; and
   control means for uniformly controlling the nitrite ion concentration in the processing liquid from the electric potential difference between said semiconductor electrode and said opposing electrode, detected by said detection means.

2. An etching device claimed in claim 1, wherein said semiconductor electrode comprises a silicon electrode and said opposing electrode comprises a platinum electrode.

3. An etching device claimed in claim 1, wherein said semiconductor electrode comprises a silicon electrode and said opposing electrode comprises a carbon electrode.

4. An etching device performing an etching process on a material immersed in the processing liquid, using a processing liquid which is a mixture of acids of which the main components are flouric acid, nitric acid, and acetic acid, the etching device comprising:
a semiconductor electrode immersed in the processing liquid;
an opposing electrode which is also immersed in the processing liquid, opposing said semiconductor electrode;
means for detecting an electric potential difference between said semiconductor electrode and said opposing electrode; and
chemical addition means for adding nitrite ions or a chemical which generates nitrite ions to the processing liquid corresponding to the electric potential difference between said semiconductor electrode and said opposing electrode, detected by the detection means.

5. An etching device claimed in claim 4, wherein said semiconductor electrode comprises a silicon electrode and said opposing electrode comprises a platinum electrode.

6. An etching device claimed in claim 4, wherein said semiconductor electrode comprises a silicon electrode and said opposing electrode comprises a carbon electrode.

7. An etching device claimed in claim 4, wherein said chemical addition means adds a nitrite solution into the processing liquid corresponding to the electric potential difference between said semiconductor electrode and said opposing electrode.

8. An etching device claimed in claim 4, wherein said chemical addition means adds a potassium nitrite into the processing liquid corresponding to the electric potential difference between said semiconductor electrode and said opposing electrode.

9. An etching device claimed in claim 4, wherein said chemical addition means adds a potassium nitrite into the processing liquid corresponding to the electric potential difference between said semiconductor electrode and said opposing electrode.

10. An etching device claimed in claim 4, wherein said chemical addition means adds a $H_2O_2$ solution into the processing liquid corresponding to the electric potential difference between said semiconductor electrode and said opposing electrode.

11. An etching device claimed in claim 4, wherein said opposing electrode is a standard electrode and said standard electrode is immersed into a saturated KCL solution and said silicon electrode is immersed into the processing liquid.

12. An etching device performing an etching process on a material immersed in the processing liquid, using a processing liquid which is a mixture of acids of which the main components are flouric acid, nitric acid, and acetic acid, the etching device comprising:
a semiconductor electrode to which a voltage is applied, immersed in the processing liquid;
an opposing electrode which is also immersed in the processing liquid, opposing said semiconductor electrode;
electric potential difference detection means for detecting an electric potential difference between said semiconductor electrode and said opposing electrode; and
voltage control means for controlling the voltage applied to said semiconductor electrode, corresponding to the electric potential difference between said semiconductor electrode and said opposing electrode, detected by said electric potential difference detection means.

13. An etching device claimed in claim 12, wherein said semiconductor electrode comprises a silicon electrode.

14. An etching device claimed in claim 12, wherein said voltage control means applies the voltage to said semiconductor electrode in order to dissolve said semiconductor electrode into the processing liquid corresponding to the electric potential difference between said semiconductor electrode and said opposing electrode detected by said electric potential difference detection means.

15. An etching device performing an etching process on a material immersed in a processing liquid, using a processing liquid comprising a mixture of acids selected from the group consisting of fluoric acid, nitric acid, and acetic acid to produce a processing liquid further comprising nitrite ions formed as the result of a dissolution reaction between said material and said processing liquid, the etching device comprising:
absorption detection means for detecting the absorption of the processing liquid; and
control means for uniformly controlling the nitrite ion concentration in the processing liquid corresponding to the absorption of the processing liquid detected by said absorption detection means.

16. An etching device as claimed in claim 15, wherein said absorption detection means comprises a spectrophotometer.

17. An etching device performing an etching process on a material immersed in the processing liquid, using a processing liquid which is a mixture of acids of which the main components are flouric acid, nitric acid, and acetic acid, the etching device, comprising:
absorption detection means for detecting the absorption of the processing liquid; and
chemical addition means for adding nitrite ions or a chemical which generates nitrite ions to the processing liquid corresponding to the absorption of the processing liquid detected by said absorption detection means.

18. An etching device as claimed in claim 17, wherein said absorption detection means comprises a spectrophotometer.

* * * * *